US011327031B2

United States Patent
Moriyasu et al.

(10) Patent No.: US 11,327,031 B2
(45) Date of Patent: May 10, 2022

(54) PHOTON COUNTING X-RAY CT APPARATUS

(71) Applicant: Canon Medical Systems Corporation, Otawara (JP)

(72) Inventors: Kenta Moriyasu, Nasushiobara (JP); Taichiro Shiodera, Shinagawa (JP); Shuhei Nitta, Ota (JP); Tomoyuki Takeguchi, Kawasaki (JP); Hidenori Takeshima, Ebina (JP); Toshiyuki Ono, Kawasaki (JP); Takashi Ida, Kawasaki (JP); Hiroaki Nakai, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 15/929,150

(22) Filed: Oct. 1, 2019

(65) Prior Publication Data
US 2020/0033273 A1 Jan. 30, 2020

Related U.S. Application Data

(62) Division of application No. 14/832,332, filed on Aug. 21, 2015, now Pat. No. 10,451,568.

(30) Foreign Application Priority Data

Aug. 22, 2014 (JP) .................................. 2014-169905
Sep. 9, 2014 (JP) .................................. 2014-183553

(51) Int. Cl.
*G01N 23/087* (2018.01)
*G01T 1/29* (2006.01)
(Continued)

(52) U.S. Cl.
CPC .......... *G01N 23/087* (2013.01); *A61B 6/032* (2013.01); *A61B 6/4035* (2013.01);
(Continued)

(58) Field of Classification Search
CPC ......... A61B 6/032; A61B 6/06; A61B 6/4035; A61B 6/4241; A61B 6/482; A61B 6/5205;
(Continued)

(56) References Cited

U.S. PATENT DOCUMENTS 6,408,050 B1 * 6/2002 Han .......................... G01T 1/17
378/98.11
7,298,812 B2 11/2007 Tkaczyk
(Continued)

FOREIGN PATENT DOCUMENTS

JP 60-75036 A 4/1985
JP 5-161633 A 6/1993
(Continued)

OTHER PUBLICATIONS

Office Action dated Apr. 9, 2019 is Japanese Patent Application No. 2015-164166 citing references AO-AQ therein.

*Primary Examiner* — Dani Fox
*Assistant Examiner* — Soorena Kefayati
(74) *Attorney, Agent, or Firm* — Oblon, McClelland, Maier & Neustadt, L.L.P.

(57) ABSTRACT

A photon counting X-ray CT apparatus according to an embodiment includes: data acquiring circuitry, and processing circuitry. The data acquiring circuitry is configured to allocate energy measured by signals output from a photon counting detector in response to incidence of X-ray photons to any of a plurality of first energy bins so as to acquire a first data group as count data of each of the first energy bins. The processing circuitry is configured to determine a plurality of
(Continued)

second energy bins obtained by grouping the first energy bins in accordance with a decomposition target material that is a material to be decomposed in a imaging region, allocate the first data group to any of the second energy bins so as to generate a second data group, and use the second data group to generate an image representing a distribution of the decomposition target material.

6 Claims, 17 Drawing Sheets

(51) Int. Cl.
| | | |
|---|---|---|
| G01N 23/046 | (2018.01) | |
| A61B 6/00 | (2006.01) | |
| A61B 6/03 | (2006.01) | |
| A61B 6/06 | (2006.01) | |

(52) U.S. Cl.
CPC ............ *A61B 6/4241* (2013.01); *A61B 6/482* (2013.01); *A61B 6/5205* (2013.01); *A61B 6/5211* (2013.01); *G01N 23/046* (2013.01); *G01T 1/2985* (2013.01); *A61B 6/06* (2013.01); *G01N 2223/402* (2013.01)

(58) Field of Classification Search
CPC ........... A61B 6/5211; G01N 2223/402; G01N 23/046; G01N 23/087; G01T 1/2985; G06T 5/002; G06T 11/005; G06T 11/003; G06T 11/008; G16H 50/20
See application file for complete search history.

(56) References Cited

U.S. PATENT DOCUMENTS

| | | | | |
|---|---|---|---|---|
| 7,663,120 B2* | 2/2010 | Tomita | ...................... | G01T 1/17 250/394 |
| 8,000,434 B2* | 8/2011 | Ziegler | ................. | G01T 1/2985 378/5 |
| 8,965,095 B2* | 2/2015 | Zou | ...................... | A61B 6/5258 382/131 |
| 9,052,266 B2 | 6/2015 | Miyazaki | | |
| 9,532,759 B2* | 1/2017 | Taguchi | ................. | G16H 50/30 |
| 9,928,585 B2 | 3/2018 | Schirra | | |
| 2004/0101086 A1 | 5/2004 | Sabol | | |
| 2005/0084069 A1* | 4/2005 | Du | ........................ | A61B 6/405 378/98.9 |
| 2006/0109949 A1* | 5/2006 | Tkaczyk | ................ | A61B 6/032 378/4 |
| 2006/0109953 A1* | 5/2006 | Walter | ................... | A61B 6/032 378/5 |
| 2006/0280281 A1 | 12/2006 | Flohr | | |
| 2007/0076842 A1* | 4/2007 | Tkaczyk | ............. | A61B 6/4042 378/5 |
| 2007/0242802 A1 | 10/2007 | Dafni | | |
| 2008/0063135 A1* | 3/2008 | DeMan | ................. | G01N 23/20 378/4 |
| 2008/0137803 A1* | 6/2008 | Wu | ........................ | A61B 6/481 378/5 |
| 2008/0273666 A1 | 11/2008 | Walter | | |
| 2009/0052612 A1* | 2/2009 | Wu | ...................... | A61B 6/4241 378/5 |
| 2009/0052621 A1* | 2/2009 | Walter | ................. | A61B 6/4035 378/53 |
| 2009/0060313 A1* | 3/2009 | Harer | ........................ | G06T 5/50 382/132 |
| 2009/0129539 A1 | 5/2009 | Licato | | |
| 2009/0161814 A1* | 6/2009 | Wu | ........................ | A61B 6/505 378/5 |
| 2009/0257549 A1 | 10/2009 | Heismann | | |
| 2009/0304249 A1 | 12/2009 | Wu | | |
| 2010/0131885 A1 | 5/2010 | Licato | | |
| 2010/0135453 A1 | 6/2010 | Mendonca | | |
| 2010/0135564 A1 | 6/2010 | Thomsen | | |
| 2010/0189214 A1* | 7/2010 | Shibata | ................ | A61B 6/5241 378/21 |
| 2010/0226474 A1 | 9/2010 | Yamakawa et al. | | |
| 2011/0096905 A1* | 4/2011 | Roessl | ................... | A61B 6/482 378/62 |
| 2011/0150183 A1 | 6/2011 | Wu | | |
| 2011/0194668 A1 | 8/2011 | Kanno | | |
| 2011/0243413 A1* | 10/2011 | Tkaczyk | ................ | A61B 6/032 382/131 |
| 2012/0087463 A1 | 4/2012 | Greenberg | | |
| 2013/0108013 A1* | 5/2013 | Leng | ..................... | G06T 11/003 378/19 |
| 2013/0142412 A1* | 6/2013 | Oh | ........................ | A61B 6/482 382/132 |
| 2013/0182818 A1* | 7/2013 | Miyazaki | ............. | A61B 6/4241 378/5 |
| 2013/0208856 A1 | 8/2013 | Klein | | |
| 2013/0308847 A1* | 11/2013 | Schirra | ................ | G06T 11/005 382/131 |
| 2014/0023181 A1* | 1/2014 | Noshi | ..................... | A61B 6/482 378/98 |
| 2014/0037045 A1* | 2/2014 | Dafni | ..................... | G01T 1/2985 378/5 |
| 2014/0086382 A1* | 3/2014 | Flohr | ................... | A61B 6/4035 378/5 |
| 2014/0133729 A1* | 5/2014 | Goshen | ................ | A61B 6/5205 382/131 |
| 2014/0185896 A1* | 7/2014 | Baturin | ................ | A61B 6/5217 382/131 |
| 2014/0233693 A1* | 8/2014 | Wang | ................... | A61B 6/5294 378/5 |
| 2015/0038827 A1 | 2/2015 | Yamagata | | |
| 2015/0103970 A1* | 4/2015 | Chen | ..................... | A61B 6/484 378/5 |
| 2015/0131883 A1* | 5/2015 | Taguchi | ................ | A61B 6/032 382/131 |
| 2015/0182176 A1* | 7/2015 | Jin | .......................... | G01T 1/171 378/5 |
| 2015/0265227 A1* | 9/2015 | Sano | ..................... | A61B 6/542 378/64 |
| 2015/0348292 A1* | 12/2015 | Taguchi | ................ | A61B 6/032 382/131 |
| 2016/0081637 A1* | 3/2016 | Noshi | ................... | G01T 1/2985 378/5 |
| 2016/0086358 A1* | 3/2016 | Leng | ..................... | A61B 6/032 378/19 |
| 2017/0023496 A1* | 1/2017 | Persson | ................ | G06T 11/005 |
| 2018/0214113 A1* | 8/2018 | Yamakawa | .......... | G01N 23/083 |

FOREIGN PATENT DOCUMENTS

| | | |
|---|---|---|
| JP | 2009-17984 A | 1/2009 |
| JP | 2010-5272 A | 1/2010 |
| JP | 2010-253138 A | 11/2010 |
| JP | 2011-244875 A | 12/2011 |
| JP | 2012-34901 A | 2/2012 |
| JP | 5367574 B2 | 9/2013 |
| JP | 2014-36836 A | 2/2014 |
| JP | 2014-503331 A | 2/2014 |
| JP | 2014-117568 A | 6/2014 |
| JP | 2014-138796 A | 7/2014 |
| WO | WO 2009/022625 A1 | 2/2009 |
| WO | WO 2012/009725 A1 | 1/2012 |

* cited by examiner

FIG.2
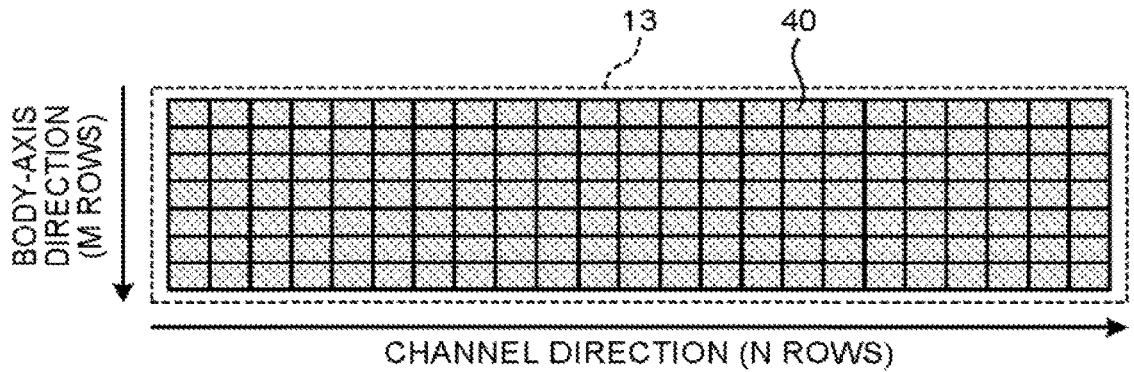
FIG.3
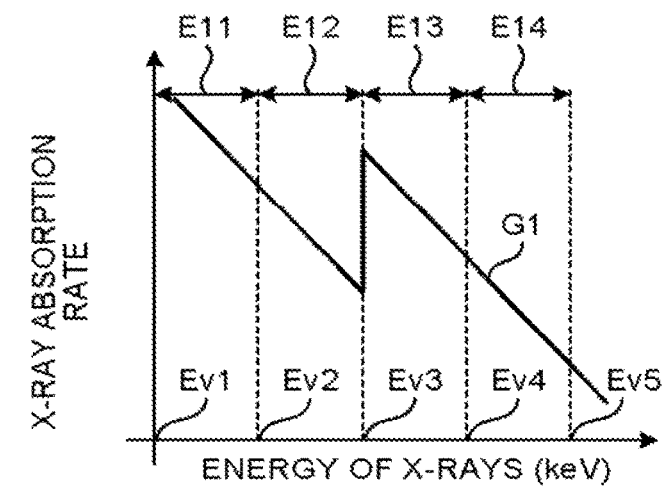
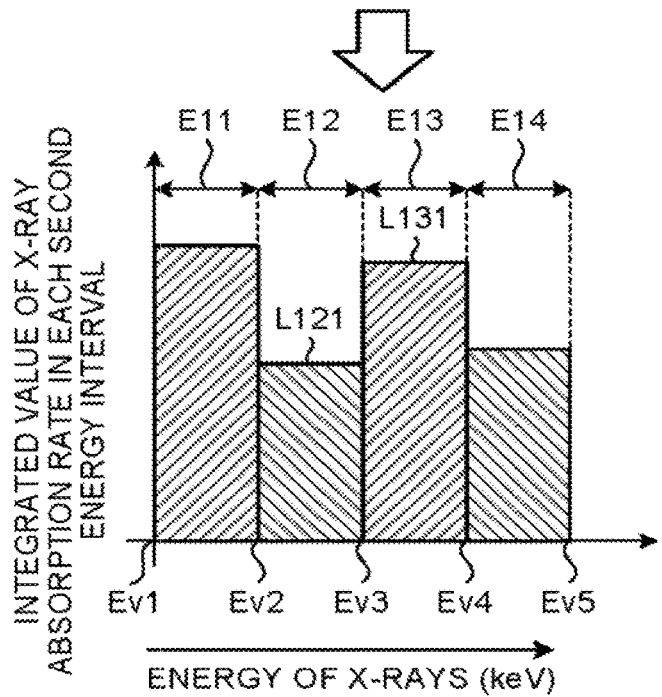

PHOTON COUNTING X-RAY CT APPARATUS

CROSS-REFERENCE TO RELATED APPLICATIONS

This application is a divisional application of U.S. patent Ser. No. 14/832,332, filed Aug. 25, 2015, which is based upon and claims the benefit of priority of the prior Japanese Patent Application No. 2014-169905, filed on Aug. 22, 2014, and the prior Japanese Patent Application No. 2014-183553, filed on Sep. 9, 2014, the entire contents of each of which are incorporated herein by reference. The entire contents of the prior Japanese Patent Application No. 2015-164166, filed on Aug. 21, 2015, is also incorporated herein by reference.

FIELD

Embodiments described herein relate generally to a photon counting X-ray computed tomography (CT) apparatus.

BACKGROUND

As an application of X-ray computed tomography (CT), a technique is available in which differences in X-ray absorption characteristics among materials are utilized to discriminate, for example, types, amounts, and densities of materials contained in a subject. This is called material decomposition. Increasing the monochromaticity of X-rays used for the material decomposition increases the difference in interaction between a certain material and other materials. For this reason, highly monochromatic X-rays, that is, X-rays with a narrow energy range are preferably used to perform the accurate material decomposition.

However, increasing the monochromaticity of X-rays used for the material decomposition reduces the number of photons of the X-rays, so that the material decomposition becomes susceptible to noise. The dose of X-rays irradiating the subject needs to be reduced, so that the number of photons of the X-rays is difficult to be increased to avoid the influence of noise. For this reason, the conventional material decomposition with the X-ray CT is difficult to accurately discriminate, for example, types, amounts, and densities of materials contained in the subject.

BRIEF DESCRIPTION OF THE DRAWINGS

FIG. 2 is a drawing for explaining an example of a detector according to the first embodiment;

FIG. 3 is a diagram for explaining optimal energy bins set for decomposition target material:

DETAILED DESCRIPTION

A photon counting X-ray CT apparatus according to an embodiment includes: data acquiring circuitry, and processing circuitry. The data acquiring circuitry is configured to allocate energy measured by signals output from a photon counting detector in response to incidence of X-ray photons to any of a plurality of first energy bins so as to acquire a first data group as count data of each of the first energy bins. The processing circuitry is configured to determine a plurality of second energy bins obtained by grouping the first energy bins in accordance with a decomposition target material that is a material to be decomposed in a imaging region, allocate the first data group to any of the second energy bins so as to generate a second data group, and use the second data group to generate an image representing a distribution of the decomposition target material.

The following explains a photon counting X-ray computed tomography (CT) apparatus according to embodiments, with reference to the accompanying drawings.

First Embodiment

Figure 1:
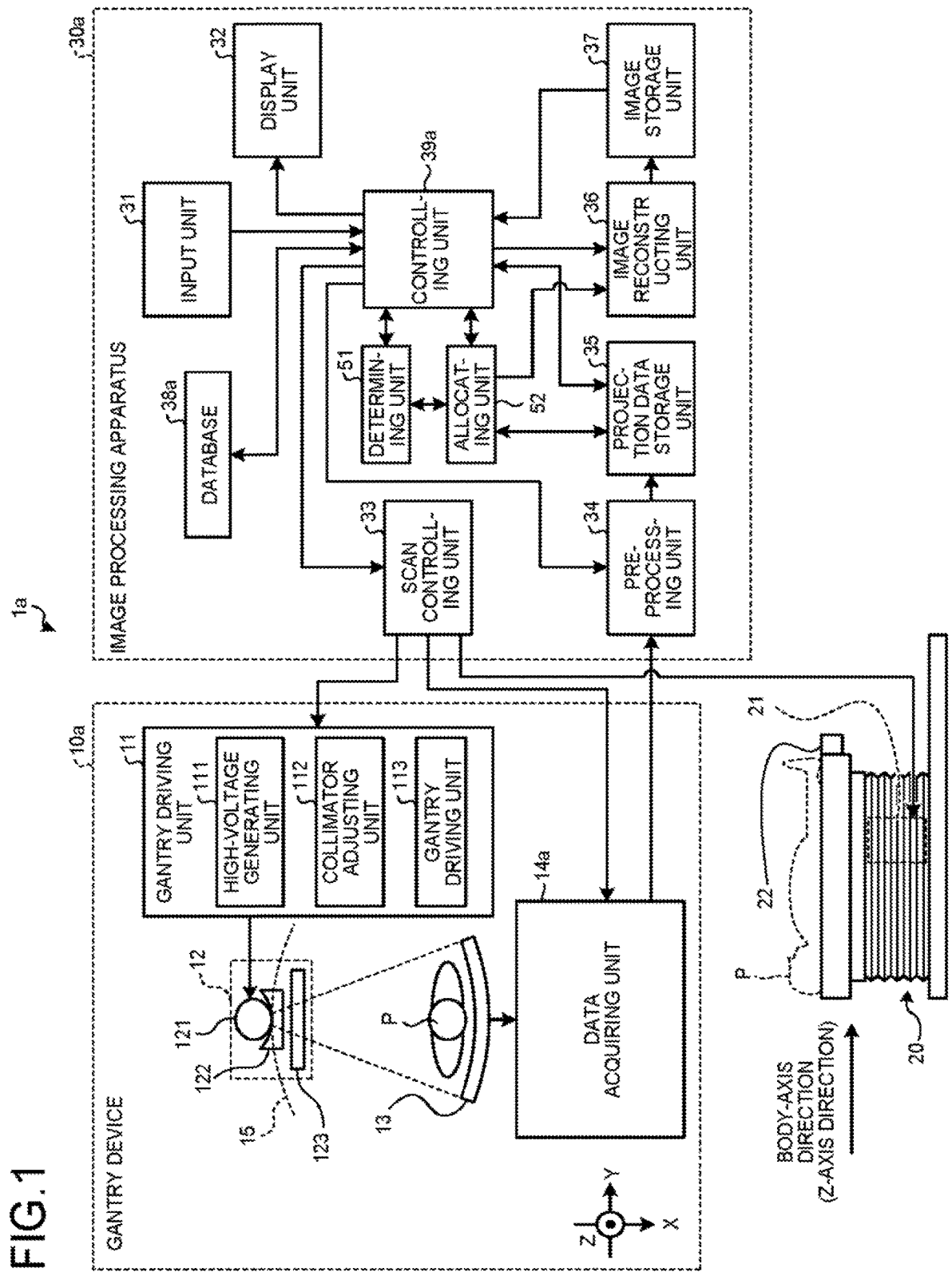
FIG. 1 is a diagram of an exemplary configuration of a photon counting X-ray CT apparatus according to a first embodiment.

First, a configuration of a photon counting X-ray CT apparatus 1a according to a first embodiment will be explained. FIG. 1 is a diagram of an exemplary configuration of the photon counting X-ray CT apparatus 1a according to the first embodiment. As illustrated in FIG. 1, the photon counting X-ray CT apparatus 1a according to the first embodiment includes a gantry device 10a, a couch device 20, and an image processing apparatus 30a.

The gantry device 10a irradiates a subject P with X-rays and acquires projection data (to be explained later). The gantry device 10a includes a gantry controlling unit 11, an X-ray generating device 12, a detector 13, a data acquiring unit 14a, and a rotating frame 15.

Under the control of a scan controlling unit 33 (to be explained later), the gantry controlling unit 11 controls operations of the X-ray generating device 12 and the rotating frame 15. The gantry controlling unit 11 includes a high-voltage generating unit 111, a collimator adjusting unit 112, and a gantry driving unit 113. The high-voltage generating unit 111 supplies an X-ray tube voltage to an X-ray tube 121 (to be explained later). The collimator adjusting unit 112 adjusts the aperture and the position of a collimator 123 to adjust the irradiation range of X-rays emitted from the X-ray generating device 12 to the subject P. For example, the collimator adjusting unit 112 adjusts the aperture of the collimator 123 to adjust the irradiation range of the X-rays, that is, the fan angle and the cone angle. The gantry driving unit 113 drives to rotate the rotating frame 15 to turn the X-ray generating device 12 and the detector 13 on circular orbits centered on the subject P.

The X-ray generating device 12 generates the X-rays for irradiating the subject P. The X-ray generating device 12 includes the X-ray tube 121, a wedge 122, and the collimator 123. The X-ray tube 121 generates the X-rays. The X-ray tube 121 emits the beam-shaped X-rays for irradiating the subject P at the X-ray tube voltage supplied by the high-voltage generating unit 111. The X-ray tube 121 is a vacuum tube that generates the beam-shaped X-rays widening in a cone shape or a pyramid shape along the body-axis direction of the subject P. The beam-shaped X-rays are also called a cone beam. The X-ray tube 121 irradiates the subject P with the cone beam along with the rotation of the rotating frame 15. The wedge 122 is an X-ray filter for adjusting the X-ray dose of the X-rays emitted from the X-ray tube 121. The collimator 123 is slits for narrowing down, under the control of the collimator adjusting unit 112, the irradiation range of the X-rays with the X-ray dose adjusted by the wedge 122.

The detector 13 includes a plurality of detecting elements that count the number of photons of the X-rays that have passed through the subject P. In one example, the detecting elements included in the detector 13 according to the first embodiment are cadmium-telluride-based semiconductors. In other words, the detector 13 according to the first embodiment is a direct-conversion-type semiconductor detector that counts the light beams derived from the X-rays by directly converting the incident X-rays to the light beams.

FIG. 2 is a drawing for explaining an example of the detector. For example, the detector 13 according to the first embodiment is, as illustrated in FIG. 2, an area detector in which detecting elements 40 formed with cadmium telluride are arranged in N rows along the channel direction (the Y-axis direction in FIG. 1) and are arranged in M rows along the body-axis direction (the Z-axis direction in FIG. 1). When a photon has become incident thereto, each of the detecting elements 40 outputs an electric signal of one pulse. By discriminating each of the pulses output by the detecting elements 40, it is possible to count the number of photons (X-ray photons) derived from the X-rays that have become incident to the detecting elements 40. Further, by performing a calculating process based on the strength of each of the pulses, it is possible to measure the energy levels of the counted photons.

The following explains a case in which the detector 13 is the direct-conversion-type semiconductor detector. The first embodiment is, however, also applicable to a case in which an indirect-conversion-type detector constituted by scintillators and photodetectors is used as the detector 13. The photodetectors are, for example, photomultiplier tubes or silicon photomultipliers (SiPMs) including avalanche photodiodes (APDs).

The data acquiring unit 14a acquires the data group obtained by allocating the energy measured by the signals output from the photon counting detector 13 according to the incidence of the X-ray photons to the energy bins. Specifically, the data acquiring unit 14a according to the first embodiment allocates the energy measured by the signals output from the photon counting detector 13 according to the incidence of the X-ray photons to any of the first energy bins so as to acquire the first data group serving as the count data of each of the first energy bins. For example, the minimum number of energy bins settable by the data acquiring unit 14a is set as the first energy bins. For example, the data acquiring unit 14a performs analog/digital (A/D) conversion to convert pulses serving as analog data output from the detector 13 into digital data, and allocates the result to the first energy bins set as a sufficient number of energy bins (intervals).

The data acquiring unit 14a acquires, for each of phases of the X-ray tube 121 (X-ray tube phases, views), incident positions (detection positions) of the X-ray photons counted by discriminating the pulses output by the detecting elements 40 and energy of the X-ray photons, as the counting result. For example, the data acquiring unit 14a uses the positions of the detecting elements 40 that output the pulses used in the counting process as the incident positions. Further, for example, the data acquiring unit 14a calculates the energy from a peak value of the pulses and a response function unique to the system. Alternatively, for example, the data acquiring unit 14a may calculate the energy by integrating the strengths of the pulses.

The data acquiring unit 14a then allocates the counting result to any of the first energy bins so as to acquire the first data group. The first data group serves as, for example, information indicating the following: in an X-ray tube phase "α1", the count value of photons having an energy range "E1L to E1R" is "n1", and the count value of photons having an energy range "E2L to E2R" is "n2", at one of the detecting elements 40 in an incident position "P11". Alternatively, the first data group serves as information indicating the following counting result: in the X-ray tube phase "α1", the count value of photons per unit time having the energy range "E1L to E1R" is "n1", and the count value of photons per unit time having the energy range "E2L to E2R" is "n2", at one of the detecting elements 40 in the incident position "P11".

The first energy bins may be, for example, energy bins determined by energy resolution. In such a case, the counting result serves as data constituting the first data group, and the first data group serves as, for example, information indicating the following: in the X-ray tube phase "α1", the count value of photons having an energy level "E1" is "NN1", at one of the detecting elements 40 in the incident position "P11". For example, if the detector 13 is an indirect-conversion-type detector including SiPMs, and a detector system is used that outputs digital data indicating the result of the energy decomposition, the data acquiring unit 14a acquires the data output from the detector 13 as the first data group.

The rotating frame 15 is an annular frame that supports the X-ray generating device 12 and the detector 13 so as to face each other with the subject P interposed therebetween. The rotating frame 15 is driven by the gantry driving unit 113, and rotates at a high speed on a circular orbit centered on the subject P.

The couch device 20 is a device on which the subject P is placed and includes a couchtop 22 and a couch driving device 21. The couchtop 22 is a plate on which the subject P is placed. The couch driving device 21 moves the couchtop 22 in the Z-axis direction so as to move the subject P into the rotating frame 15.

For example, the gantry device 10a performs a helical scan, which is to helically scan the subject P by causing the rotating frame 15 to rotate while moving the couchtop 22. In another example, the gantry device 10a performs a conventional can, which is to scan the subject P on the circular trajectory by causing the rotating frame 15 to rotate while the subject P is fixed in a position after the couchtop 22 has been moved. In yet another example, the gantry device 10a implements a step-and-shoot method by which the conventional scan is performed in a plurality of scan areas by moving the couchtop 22 to positions arranged at regular intervals.

The image processing apparatus 30a is a device that receives an operation performed on the photon counting X-ray CT apparatus 1a by a user, and that reconstructs a CT image using the data group based on the counting result acquired by the gantry device 10a. As illustrated in FIG. 1, the image processing apparatus 30a includes an input unit 31, a display unit 32, the scan controlling unit 33, a pre-processing unit 34, a projection data storage unit 35, an image reconstructing unit 36, an image storage unit 37, a database 38a, a controlling unit 39a, a determining unit 51, and an allocating unit 52.

The input unit 31 includes, for example, a mouse and a keyboard used by the user of the photon counting X-ray CT apparatus 1a to enter various types of instructions and various types of settings, and transfers the information on the instructions and the settings received from the user to the controlling unit 39a. For example, the input unit 31 receives reconstruction conditions for reconstructing the CT image, image processing conditions for the CT image, and the like, from the user.

The display unit 32 is a monitor referred to by the user. Under the control of the controlling unit 39a, the display unit 32 displays the CT image for the user, and displays a graphical user interface (GUI) for receiving, for example, the various types of instructions and the various types of settings from the user via the input unit 31.

Under the control of the controlling unit 39a, the scan controlling unit 33 controls operations of the gantry controlling unit 11, the data acquiring unit 14a, and the couch driving device 21. Specifically, the scan controlling unit 33 controls the gantry controlling unit 11 so as to rotate the rotating frame 15, emit the X-rays from the X-ray tube 121, and adjust the aperture and the position of the collimator 123, when the photon counting CT imaging is performed. Under the control of the controlling unit 39a, the scan controlling unit 33 also controls the data acquiring unit 14a. Under the control of the controlling unit 39a, the scan controlling unit 33 further controls the couch driving device 21 to move the couchtop 22 when the subject P is imaged.

The pre-processing unit 34 generates the projection data by applying correcting processes, such as a logarithmic transformation process, an offset correction, a sensitivity correction, and a beam hardening correction, to the data group transmitted from the data acquiring unit 14a. In the present embodiment, the pre-processing unit 34 generates the projection data from the first data group described above.

The projection data storage unit 35 stores the projection data generated from the first data group by the pre-processing unit 34. In the following description, the projection data generated from the first data group will be called "first projection data group".

The determining unit 51 determines the second energy bins obtained by grouping the first energy bins according to the decomposition target material that is material to be decomposed in an imaging region. As a grouping procedure, a grouping is performed so that, for example, a certain energy level unique to each of the decomposition target materials substantially coincides with a boundary between adjacent ones of the second energy bins. In other words, based on the energy information unique to each of the decomposition target materials, the determining unit 51 determines the second energy bins optimal for decomposing the decomposition target material. The determining unit 51 obtains predetermined information for determining the second energy bins from the input unit 31 or the database 38a via the controlling unit 39a. For example, the determining unit 51 receives a user operation for selecting the decomposition target material from candidate decomposition target materials, from the input unit 31 or the like via the controlling unit 39a. The determining unit 51 notifies the allocating unit 52 of the information on the determined second energy bins. A process to determine the second energy bins will be explained later. The grouping procedure is stored, for example, in the controlling unit 39a. The determining unit 51 may obtain a pattern of the grouping procedure from the controlling unit 39a, as needed.

The allocating unit 52 allocates the first data group to any of the second energy bins so as to generate the second data group. In the present embodiment, the allocating unit 52 allocates the first projection data group to any of the second energy bins so as to generate a second projection data group. A method for generating the second data group (second projection data group) will be explained later. The allocating unit 52 obtains the first projection data group from the projection data storage unit 35, and obtains the information on the second energy bins from the determining unit 51. The allocating unit 52 performs the allocating process to generate the second projection data group, and then, transmits the second projection data group to the image reconstructing unit 36. The allocating unit 52 can also store the second projection data group in the projection data storage unit 35.

The image reconstructing unit 36 performs a reconstructing process of the projection data group. Examples of the reconstructing process include, but are not limited to, a back-projection process using a filtered back-projection (FBP) method. The image reconstructing unit 36 generates various images from the CT image obtained by the reconstructing process. In the present embodiment, the image reconstructing unit 36 uses the second data group (second projection data group) to generate the image representing the distribution of the decomposition target material in the imaging region. In other words, the image reconstructing unit 36 generates the image highlighting the decomposition target material based on the second projection data group obtained by allocating the energy to optimal energy bins. The image reconstructing unit 36 stores the reconstructed CT image and the image generated by various types of image processing in the image storage unit 37. The image reconstructing unit 36 is also called the generating unit.

In this situation, the projection data obtained from the photon counting CT contains information about the energy of the X-rays attenuated by passing through the subject P. For this reason, the image reconstructing unit 36 is able to, for example, reconstruct CT images representing a specific energy component. Further, the image reconstructing unit 36 is able to, for example, reconstruct CT images representing each of a plurality of energy components.

Further, for example, the image reconstructing unit 36 is able to generate images in which a tone corresponding to an energy component is assigned to each of the pixels in the CT images representing the energy components, so that a plurality of pieces of CT images that are color-coded associated with the energy components are superimposed. Further, the image reconstructing unit 36 is able to generate images that make it possible to identify material by utilizing the K absorption edge unique to each material. Other examples of images generated by the image reconstructing unit 36 include monochrome X-ray images, density images, and effective atomic number images.

The database 38a is a database that stores information on an X-ray absorption spectrum of each of a plurality of materials. In other words, the database 38a is a database storing analytical chemical information. The database 38a can update and store various types of analytical chemical information using information from external analytical chemical databases. For example, the database 38a stores energy levels unique to respective elements produced in response to X-rays, as a table. In the case of a molecule or a constituent material consisting of a plurality of materials, an energy level unique to the molecule or the constituent material can be calculated from this energy table.

The controlling unit 39a performs overall control of the photon counting X-ray CT apparatus 1a by controlling operations of the gantry device 10a, the couch device 20, and the image processing apparatus 30a. Specifically, the controlling unit 39a controls the scan controlling unit 33 to control the CT scan performed by the gantry device 10a. The controlling unit 39a also controls the pre-processing unit 34 and the image reconstructing unit 36 to control the image reconstructing process and the image generating process performed by the image processing apparatus 30a. The controlling unit 39a further performs control to display the various images stored in the image storage unit 37 on the display unit 32. The controlling unit 39a controls the projection data storage unit 35, the determining unit 51, the allocating unit 52, and the image reconstructing unit 36, and serves as a medium of exchange of certain information with the database 38a, the input unit 31, and the display unit 32.

The following explains the outline of material decomposition performed by the photon counting X-ray CT apparatus according to the first embodiment.

In conventional X-ray CT apparatuses, an integrating detector obtains the intensity of X-rays integrated with respect to energy, so that information as to what materials constitute each portion in the imaged region can only be roughly known using a CT value. The photon counting X-ray CT apparatus can, however, obtain the projection data of each of the energy bins by counting the number of photons of the X-rays that have passed through the subject P, and measuring the energy levels of the counted photons. Each atom has unique quantum mechanical energy levels, and the discontinuous behavior of the X-ray absorption rate of the atom when viewed as a function of the energy corresponds to the unique energy levels. Accordingly, utilizing the energy dependence of the X-ray absorption rate allows an estimation as to what elements constitute the region in the subject P irradiated with the X-rays. When the decomposition target material is given, the photon counting X-ray CT apparatus can generate, for example, an image, such as a density distribution image of the decomposition target material, representing regions where the decomposition target material is present. Specific examples of the decomposition target material include, but are not limited to, elements such as Ca and I, molecules such as water, and constituent elements consisting of a plurality of materials, such as bones and alloys.

Consider, as an example, an interval A serving as an interval on the low-energy side and an interval B serving as an interval on the high-energy side that are adjacent to each other on both sides of a substantial boundary at a certain energy value unique to a decomposition target material. The X-ray absorption rate of the decomposition target material greatly changes between before and after the certain energy value unique to the decomposition target material. Accordingly, by generating an image A reconstructed from the projection data in the interval A and an image B reconstructed from the projection data in the interval B, and subtracting the image B from the image A, an image can be obtained in which the regions are mainly extracted that include the decomposition target materials with the greatly changing X-ray absorption rate. In another example, by reconstructing a difference projection data group by subtracting data B serving as the projection data in the interval B from data A serving as the projection data in the interval A, an image can be obtained in which the regions including the decomposition target material is mainly extracted. In still another example, a spatial density distribution of the decomposition target material may be directly obtained by setting up simultaneous equations for each of the energy bins under the assumption that only the decomposition target material is present, and solving the simultaneous equations.

The difference image described above serves as an image indicating the decomposition target material of interest for the following reason. In general, the energy dependence of the X-ray absorption rate of a material is expected to exhibit a continuous energy dependence except in the case of an energy value, such as the K absorption edge, unique to a decomposition target material. Accordingly, in the case of materials other than the decomposition target material, values obtained by, for example, subtracting the data B from the data A as described above are expected to be small values. However, in the case of the decomposition target material, the X-ray absorption rate greatly changes between before and after the energy level unique to each of the decomposition target materials, so that the values of the data A greatly differ from the values of the data B. Therefore, the values obtained by subtracting the data B from the data A are expected to be large values. As a result of the above, the difference projection data group described above has large values only when the decomposition target material is present, and has small values when the decomposition target material is not present, according to the density of the decomposition target material. Accordingly, the difference projection data group can be considered as a data group indicating signals resulting from the decomposition target material.

In this way, the photon counting X-ray CT apparatus can generate and output the image corresponding to the density distribution of the decomposition target material according to the decomposition target material (materials of interest) specified (preset) in advance.

Figure 4:
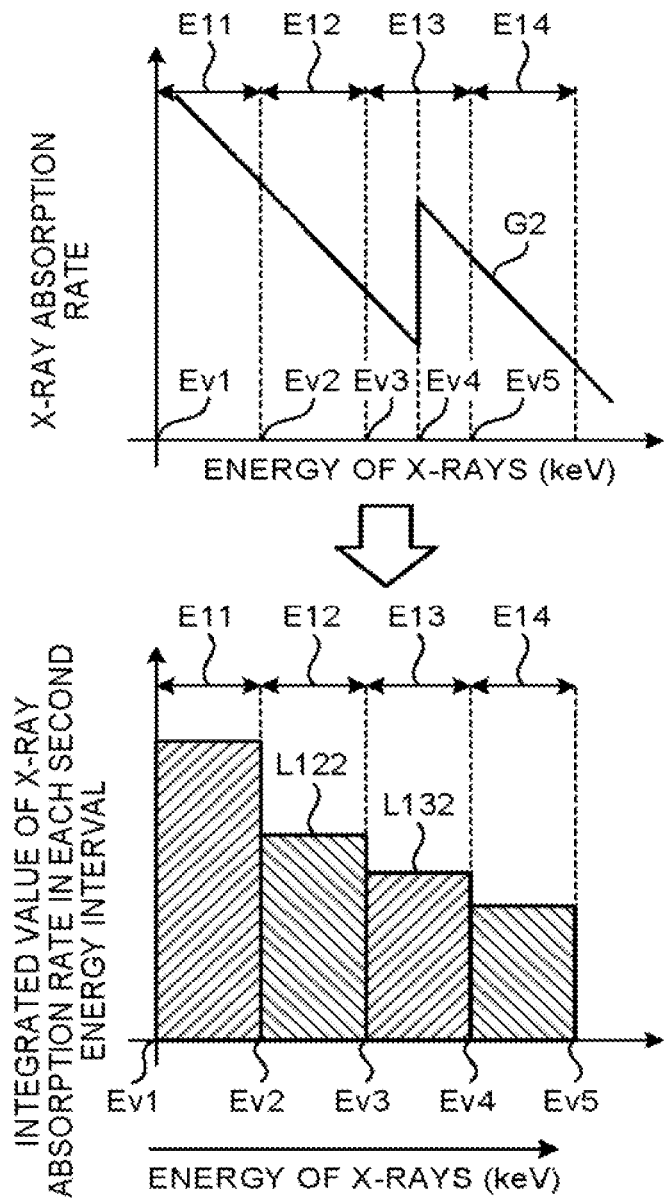
FIG. 4 is a diagram for explaining inappropriate energy bins set for the decomposition target material.

However, the energy bins optimal for the material decomposition vary depending on the decomposition target material. FIG. 3 is a diagram for explaining the optimal energy bins set for the decomposition target material, and FIG. 4 is a diagram for explaining inappropriate energy bins set for the decomposition target material.

Each atom has unique energy levels, such as the 1s orbital energy level. When an atom is irradiated with X-rays, the atom absorbs a larger amount of X-rays at energy levels corresponding to the energy levels unique to the atom. Accordingly, when the X-ray absorption rate (linear attenuation coefficient) is plotted as a function of the energy of the incident X-rays, the X-ray absorption rate discontinuously changes as the function of the energy. For example, the K absorption edge is well known as such an example. As the X-rays produce a photoelectric effect by knocking out electrons in the state bound in the is orbit, the material absorbs the X-rays corresponding to the energy in the bound state. The K absorption edge refers to an energy value unique to the material corresponding to such a state. Examples of the certain energy values unique to a decomposition target material other than the K absorption edge include L absorption edges and M absorption edges.

A graph G1 illustrated as the upper diagram of FIG. 3 is a graph illustrating an example of an expected behavior when the X-ray absorption rate of a material A is expressed as a function of the energy of the X-rays. This example illustrates that the X-ray absorption rate of the material A decreases as the energy level changes from a low-energy side toward a high-energy side, and rapidly increases at an energy value Ev3. Then, the X-ray absorption rate decreases again as the energy level changes toward a high-energy side. The energy value Ev3 is the certain energy value unique to the material A. In this example, four energy bins (an energy bin E11, an energy bin E12, an energy bin E13, and an energy bin E14) are set, where the energy value Ev3 that is the certain energy value unique to the material A substantially coincides with a boundary between adjacent energy bins.

The first energy bin E11 represents an energy bin in which the energy value is equal to or larger than an energy value Ev1 and smaller than an energy value Ev2. In the same way, the second energy bin E12 represents an energy bin in which the energy value is equal to or larger than the energy value Ev2 and smaller than the energy value Ev3; the third energy bin E13 represents an energy bin in which the energy value is equal to or larger than the energy value Ev3 and smaller than an energy value Ev4; and the fourth energy bin E14 represents an energy bin in which the energy value is equal to or larger than the energy value Ev4 and smaller than an energy value Ev5.

The lower diagram of FIG. 3 illustrates a histogram of integrated values each obtained by integrating the X-ray absorption rate of the material A over corresponding one of the energy bins E11, E12, E13, and E14. The height of a rectangle L121 and the height of a rectangle L131 respectively represent an integrated value over the energy bin E12 on the low-energy side and an integrated value over the energy bin E13 on the high-energy side, with the certain energy value Ev3 unique to the material A coinciding with the boundary between the energy bins E12 and E13. When the energy bins have a constant width, the X-ray absorption rate usually decreases with increase in the energy of the X-rays. However, the magnitude relation in the integrated values between the energy bins E12 and E13 is found to be opposite to the usual relation. This allows the material A to be appropriately picturized using the projection data of the energy bin E12 and the projection data of the energy bin E13.

FIG. 4 illustrates a case in which the energy bins E11, E12, E13, and E14 optimal for the material A are applied to a material B. A graph G2 illustrated as the upper diagram of FIG. 4 is a graph illustrating an example of an expected behavior when the X-ray absorption rate of the material B is expressed as a function of the energy of the X-rays. In the upper diagram of FIG. 4, an energy value of 80 is the certain energy value unique to the material B. In the example illustrated in the upper diagram of FIG. 4, the energy bin E13 includes the energy value Ev4 unique to the material B. In other words, in the example illustrated in the upper diagram of FIG. 4, the energy value Ev4 unique to the material B does not substantially coincide with a boundary between adjacent energy bins.

The lower diagram of FIG. 4 illustrates a histogram of integrated values each obtained by integrating the X-ray absorption rate of the material B over corresponding one of the energy bins E11, E12, E13, and E14.

The height of a rectangle L122 and the height of a rectangle L132 respectively represent an integrated value over the energy bin E12 and an integrated value over the energy bin E13 including the energy value Ev4 unique to the material B. Unlike the case in which the energy value Ev3 unique to the material A substantially coincides with the boundary between the adjacent energy bins as illustrated in FIG. 3, the case of FIG. 4 is such that the energy value Ev4 unique to the material B as a decomposition target material does not substantially coincide with a boundary between adjacent energy bins. As a result, the integrated value over the energy bin E13 of the X-ray absorption rate does not greatly differ from the integrated value over the energy bin E12 adjacent to the energy bin E13. This result indicates that the material B cannot be appropriately picturized using the projection data of the energy bin E13 and the projection data of the energy bin E12. Therefore, the energy bins optimal for discriminating the material A is inappropriate for discriminating the material B.

In other words, the above description indicates that a material can be appropriately picturized by determining the energy bins so that at least a certain energy value unique to a decomposition target material substantially coincides with a boundary between adjacent energy bins.

To achieve this, the determining unit 51 determines, from the first projection data group, the second energy bins optimal for discriminating the decomposition target materials based on the energy information unique to the decomposition target materials. Specifically, the second energy bins are energy bins obtained by grouping the first energy bins according to the decomposition target materials that are materials to be discriminated in the imaging region. As an example of the grouping procedure, the grouping is performed so that, for example, a certain energy value unique to a decomposition target material substantially coincides with a boundary between adjacent ones of the second energy bins.

Figure 5:
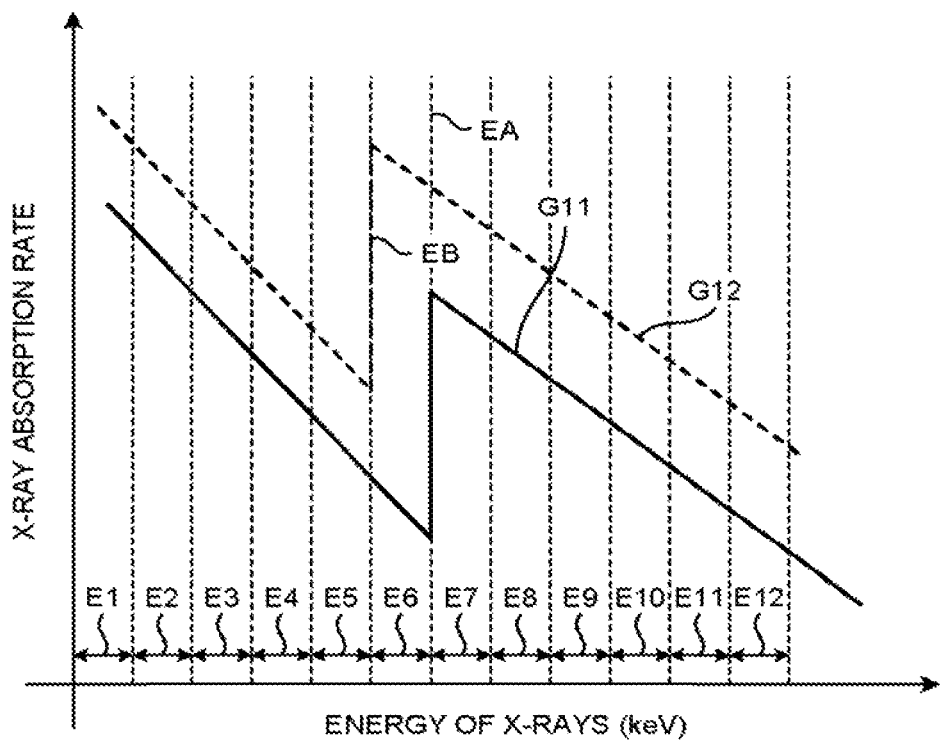
FIGS. 5 to 7 are diagrams for explaining a grouping procedure.
Figure 6:
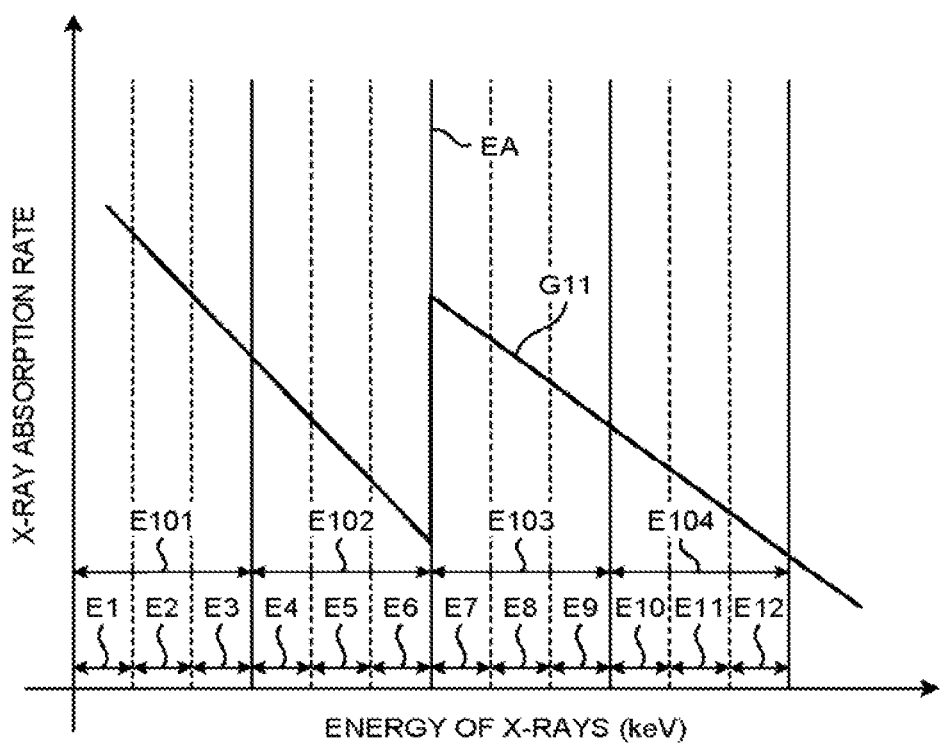
Figure 7:
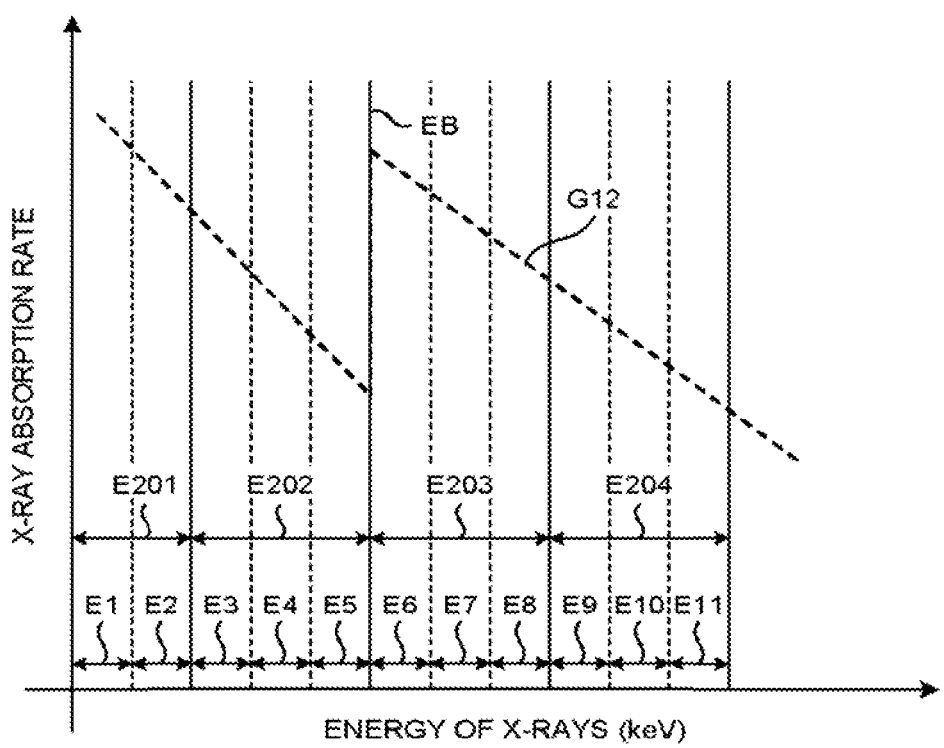

FIGS. 5 to 7 are diagrams for explaining the grouping procedure. The following assumes that the user operation using the input unit 31 has selected the two materials A and B as the decomposition target materials, and accordingly, the controlling unit 39a has obtained the energy values unique to the respective materials A and B from the database 38a and has notified the determining unit 51 of the energy values.

The first projection data group is stored in the projection data storage unit 35 as a projection data group allocated to each of the first energy bins. The dotted lines in FIG. 5 represent boundaries between the first energy bins to which the first projection data group is allocated. For example, each of the first energy bins E1 to E12 represents one of the first energy bins to which the first projection data group is allocated. The count data of the respective first energy bins is stored, first energy bins by first energy bins, as the first projection data group in the projection data storage unit 35.

In FIG. 5, a graph G11 illustrates the energy dependence of the X-ray absorption rate of the material A. The material A has a certain energy value unique to the material A at an energy level EA. A graph G12 illustrates the energy dependence of the X-ray absorption rate of the material B. The material B has a certain energy value unique to the material B at an energy level EB different from the certain energy value unique to the material A. As described above, the determining unit 51 determines the second energy bins according to the decomposition target materials. For example, the determining unit 51 determines the second energy bins so that the certain energy values unique to the decomposition target materials that are materials to be discriminated substantially coincide with boundaries between adjacent energy bins. In other words, the second energy bins are determined so that the energy level EA for the material A and the energy level EB for the material B substantially coincide with the boundaries between the second energy bins.

This determination will be explained using FIGS. 6 and 7. FIG. 6 is a diagram for explaining the grouping procedure (grouping process) in the case in which the material A is selected as a decomposition target material. Energy bins E101, E102, E103, and E104 are the second energy bins each determined for the material A. The first energy bins are bundled into the second energy bins through the grouping procedure. For example, the first energy bins E1, E2, and E3 are bundled into the second energy bin E101. The same applies to the other intervals.

As an example of a method for generating an image in which regions including the material A are mainly extracted, the image reconstructing unit 36 generates, for example, an image A1 reconstructed from second projection data of the second energy bin E102 and an image A2 reconstructed from second projection data of the second energy bin E103. The image reconstructing unit 36 then subtracts the image A2 from the image A1, and thus can obtain the image in which the regions including the material A are mainly extracted.

FIG. 7 is a diagram for explaining the grouping procedure in the case in which the material B is selected as a decomposition target material. Energy bins E201, E202, E203, and E204 are the second energy bins each determined for the material B. The first energy bins are bundled into the second energy bins through the grouping procedure. For example, the first energy bins E3, E4, and E5 are bundled into the second energy bin E202. The same applies to the other intervals.

As an example of a method for generating an image in which regions including the material B are mainly extracted, the image reconstructing unit 36 generates, for example, an image B1 reconstructed from second projection data of the second energy bin E202 and an image B2 reconstructed from second projection data of the second energy bin E203. The image reconstructing unit 36 then subtracts the image B2 from the image B1, and thus can obtain the image in which the regions including the material B are mainly extracted.

For the grouping procedure, FIGS. 6 and 7 illustrate the examples in which the second energy bins are arranged at regular intervals. The embodiments are, however, not limited to these examples. For example, in the present embodiment, the grouping procedure may be set so that the second energy bins are arranged at irregular intervals.

In another example, the grouping procedure may be set by selecting the width of each of the second energy bins so that the second energy bins have roughly the same integrated value of the X-ray absorption rate as one another. In still another example, the grouping procedure may be set so that each of the second energy bins has a larger width if the intensity of the X-rays is lower, and hence, the signal-to-noise ratio is expected to be lower in that energy bin unless the width thereof is increased.

The example has been illustrated in which the second energy bins are determined by using the whole energy range as the second energy bins. The embodiments are, however, not limited to this example. For example, the second energy bins may be determined to include only two second energy bins in which a certain energy value unique to a decomposition target material substantially coincides with a boundary between the adjacent energy bins, and data of the other energy range may be excluded from use for reconstructing the image.

In another example, the second energy bins may be determined to include only a certain number of second energy bins having energy values close to certain energy values unique to decomposition target materials, and data of the other energy range may be excluded from use for reconstructing the image. In still another example, the second energy bins may be determined to include only second energy bins corresponding to energy values caused by the incident X-rays having certain intensity or higher, and data of the other energy range may be excluded from use for reconstructing the image.

Figure 8:
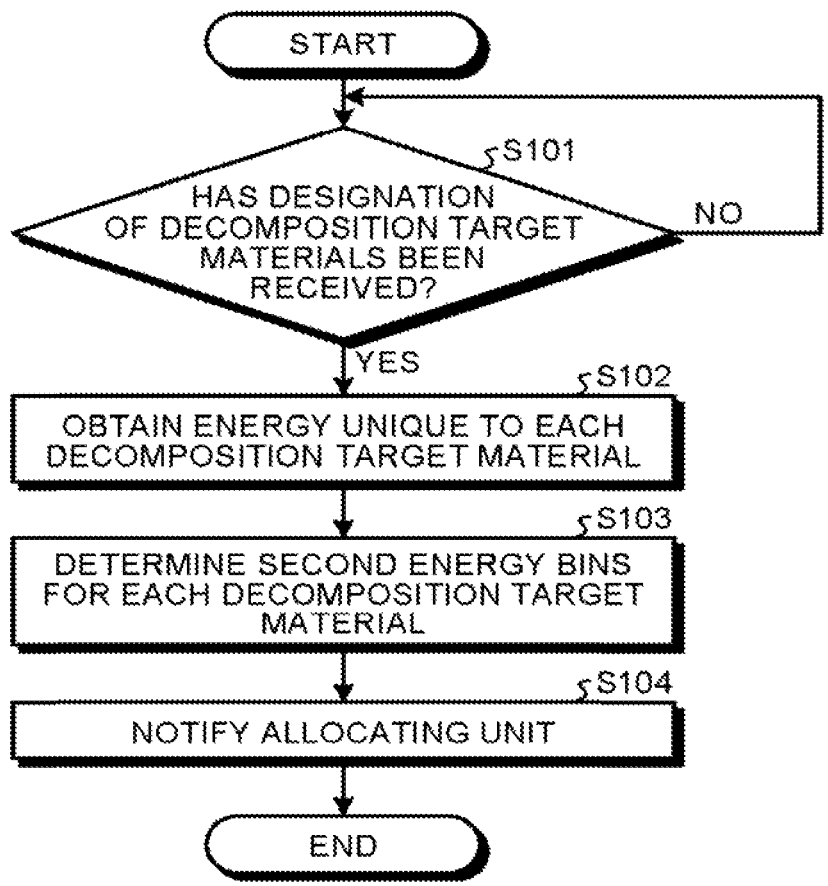
FIG. 8 is a flowchart of an example of a determining process of a plurality of second energy bins according to the first embodiment.

The following explains, using FIG. 8, a process of the determining unit 51 started by receiving a designation of the decomposition target materials. FIG. 8 is a flowchart of an example of the determining process of the second energy bins according to the first embodiment. As illustrated in FIG. 8, the controlling unit 39*a* determines whether a designation of decomposition target material has been received (step S101). If no designation has been received (No at step S101), the controlling unit 39*a* waits until a designation of decomposition target material is received. If a designation of decomposition target material has been received (Yes at step S101), the controlling unit 39*a* transmits, to the database 38*a*, a signal requesting to transmit the energy value unique to each of the designated decomposition target materials. After receiving the signal from the controlling unit 39*a*, the database 38*a* searches the database to obtain the unique energy value corresponding to each of the decomposition target materials, and transmits the value to the controlling unit 39*a*. As a result, the controlling unit 39*a* obtains the energy value unique to each of the decomposition target materials (step S102). The controlling unit 39*a* transmits the obtained energy value unique to each of the decomposition target materials to the determining unit 51.

After receiving the energy value unique to each of the decomposition target materials from the controlling unit 39*a*, the determining unit 51 determines the second energy bins for each of the decomposition target materials (step S103). After determining the second energy bins, the determining unit 51 notifies the allocating unit 52 of the result (step S104), and ends the process.

Figure 9:
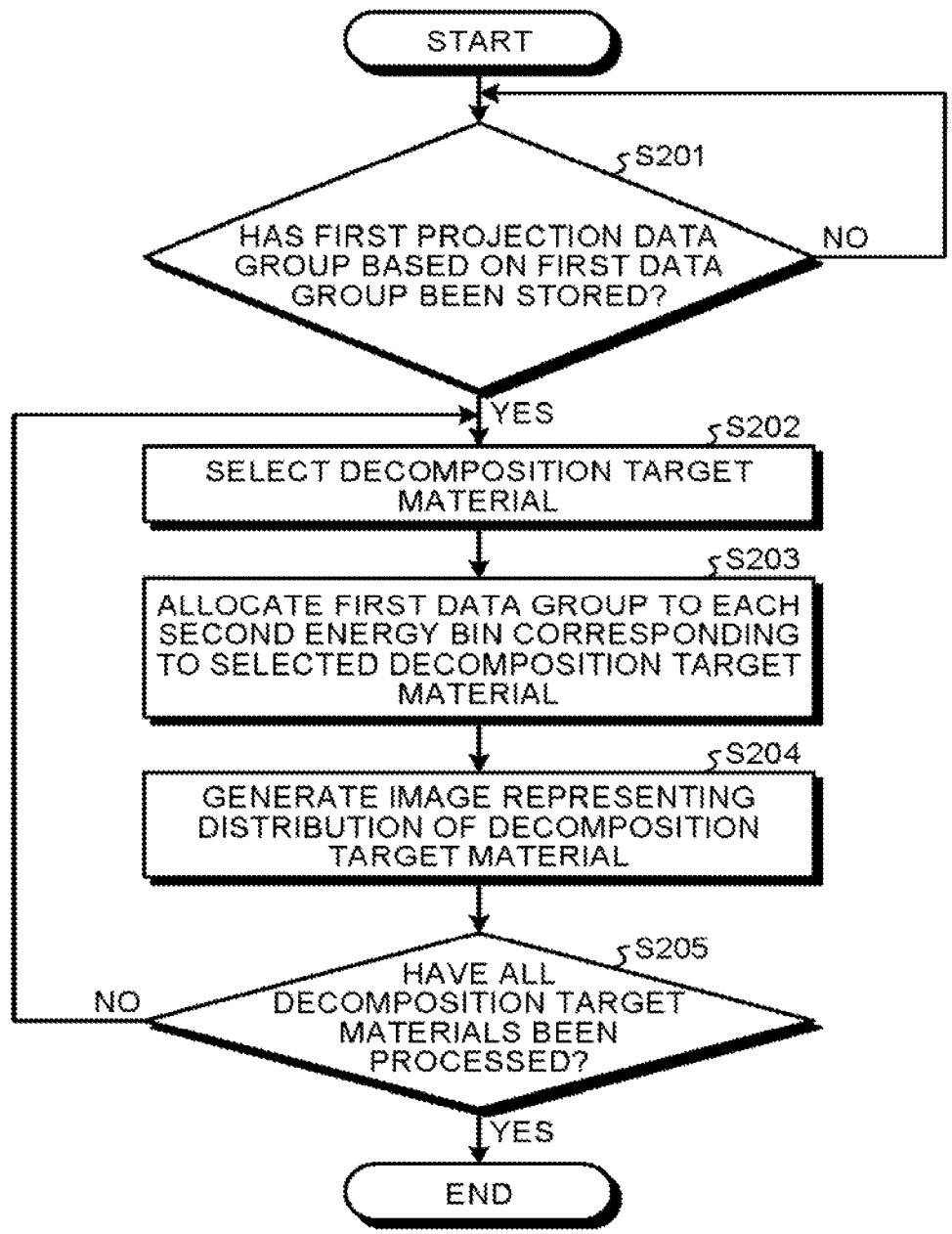
FIG. 9 is a flowchart of an example of an image generating process according to the first embodiment.

The following explains, using FIG. 9, the image generating process performed after the second energy bins are determined. FIG. 9 is a flowchart of an example of the image generating process according to the first embodiment.

As illustrated in FIG. 9, the controlling unit 39*a* determines whether the first projection data group based on the first data group has been stored in the projection data storage unit 35 (step S201). If the first projection data group has not been stored (No at step S201), the controlling unit 39*a* waits until the first projection data group is stored in the projection data storage unit 35.

If the first projection data group has been stored in the projection data storage unit 35 (Yes at step S201), the determining unit 51 selects one of the decomposition target materials (step S202). The allocating unit 52 allocates the first data group to each of the second energy bins corresponding to the selected decomposition target material, based on the second energy bins determined by the determining unit 51 (step S203). The image reconstructing unit 36 generates an image based on the data divided into the second energy bins by the allocating unit 52 (step S204). The generated image is displayed on the display unit 32 as needed.

After the image for the decomposition target material selected at step S202 is reconstructed, the controlling unit 39a determines whether all the decomposition target material have been processed (step S205). If the controlling unit 39a determines that all the decomposition target materials have been processed (Yes at step S205), the series of processing ends. If the controlling unit 39a determines that any of the decomposition target material has not been processed (No at step S205), the process returns to step S202, and the determining unit 51 selects one of the decomposition target materials (step S202). This series of processing is continued until the controlling unit 39a determines "Yes" at step S205.

As described above, in the first embodiment, the energy bins are grouped so that the certain energy values unique to the decomposition target material substantially coincide with boundaries between adjacent energy bins, and the image is reconstructed in which the material is decomposed based on the energy in the grouped energy bins. As a result, the spatial density distribution image of the decomposition target materials (materials of interest) can be generated.

Second Embodiment

The following explains a second embodiment. In the first embodiment, the case has been explained in which the image generating process is applied to all the materials designated as the material to be decomposed. In contrast, in the second embodiment, the CT value is obtained through the same reconstruction as that performed by a CT apparatus using the integrating detector, and if a material designated as a material to be decomposed is determined to be present in the imaging region, the image generating process is performed.

The image reconstructing unit 36 of the photon counting X-ray CT apparatus according to the second embodiment generates the CT image by performing the reconstructing process using all or a part of the first data group. The determining unit 51 of the photon counting X-ray CT apparatus according to the second embodiment determines whether a decomposition target material is present in the imaging region based on CT values of the CT image and the CT value corresponding to the decomposition target material, and determines the second energy bins if the decomposition target material is present in the imaging region. If the determining unit 51 determines that the decomposition target material is present, the image reconstructing unit 36 of the photon counting X-ray CT apparatus according to the second embodiment generates the image representing the distribution of the decomposition target material.

Figure 10:
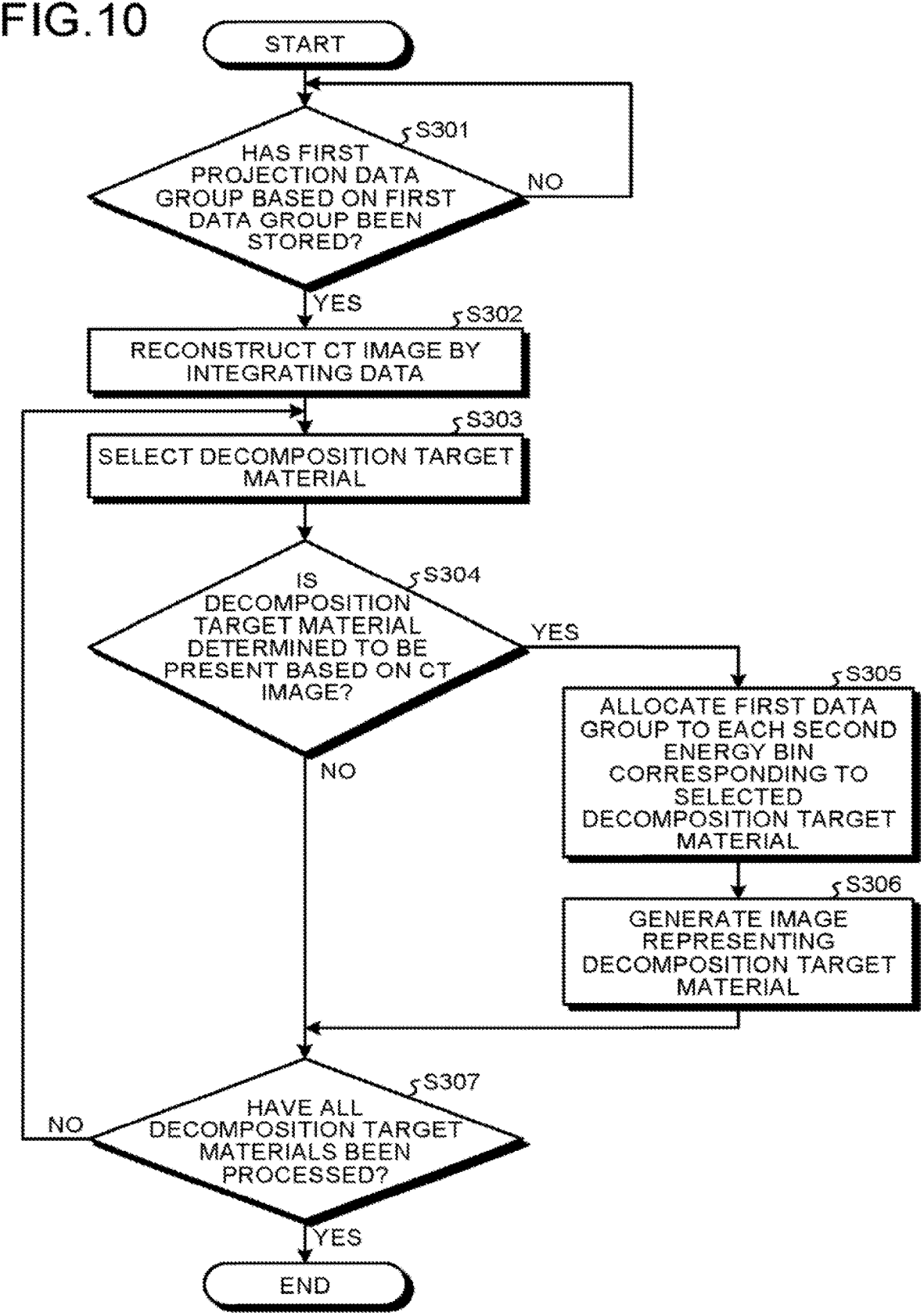
FIG. 10 is a flowchart for explaining an example of an X-ray CT process according to a second embodiment.

The above-described process will be explained using FIG. 10. FIG. 10 is a flowchart for explaining an example of the process of the photon counting X-ray CT apparatus according to the second embodiment. The determining process of the second energy bins is the same as that explained in the flowchart of FIG. 8 in the first embodiment, so that the explanation thereof will be omitted.

As illustrated in FIG. 10, the controlling unit 39a of the photon counting X-ray CT apparatus according to the second embodiment determines whether the first projection data group based on the first data group has been stored in the projection data storage unit 35 (step S301). If the first projection data group based on the first data group has not been stored (No at step S301), the controlling unit 39a waits until the first projection data group is stored in the projection data storage unit 35.

If the first projection data group has been stored in the projection data storage unit 35 (Yes at step S301), the determining unit 51 transmits, to the image reconstructing unit 36, a signal requesting to reconstruct the CT image. After receiving the request signal from the determining unit 51, the image reconstructing unit 36 obtains the first projection data group from the projection data storage unit 35. The image reconstructing unit 36 reconstructs the CT image from the projection data group generated by performing integration over all or some of the energy bins based on the first projection data group (step S302). This step will be explained later.

After generating the CT image, the image reconstructing unit 36 notifies the determining unit 51 of the result. The image reconstructing unit 36 may display the reconstructed CT image on the display unit 32 as needed.

Then, the determining unit 51 selects one of the decomposition target materials (step S303). At this step, the determining unit 51 may receive an input of the user from the input device 31 via the controlling unit 39a, and select one of the decomposition target materials based on the result of the input. Based on the CT values of the CT image and the CT value corresponding to the decomposition target material, the determining unit 51 determines whether the decomposition target material is present in the imaging region (step S304). This step will be explained later. If the determining unit 51 determines that the decomposition target material is not present in the imaging region (No at step S304), the controlling unit 39a determines that it is no use to allocate the first projection data group to the second energy bins and further perform the image reconstruction because the decomposition target material is not present in the imaging region, and ends the processing for the decomposition target material. Then, the process goes to step S307.

If the determining unit 51 determines that the decomposition target material is present in the imaging region (Yes at step S304), the allocating unit 52 allocates the first data group to each of the second energy bins corresponding to the selected decomposition target material, based on the second energy bins determined by the determining unit 51 (step S305). The allocating unit 52 notifies the image reconstructing unit 36 of the generated second data group. After obtaining the second projection data group from the allocating unit 52, the image reconstructing unit 36 uses the second projection data group to generate the image representing the distribution of the decomposition target material in the imaging region (step S306). The image reconstructing unit 36 may store the generated image in the image storage unit 37, or may cause the display unit 32 to display the generated image via the controlling unit 39a, as needed. After completing reconstructing the image for the decomposition target material, the image reconstructing unit 36 notifies the controlling unit 39a of the result of the reconstruction.

After step S304 has resulted in "No" or step S306 is completed, the controlling unit 39a determines whether all the decomposition target materials have been processed (step S307). Where needed, the controlling unit 39a may receive an input of the user via the input unit 31, and may determine based on the result of the input, whether all the decomposition target materials have been processed. If the controlling unit 39a determines that all the decomposition target materials have been processed (Yes at step S307), the photon counting X-ray CT apparatus according to the second embodiment ends the process. If the controlling unit 39a determines that any of the decomposition target material has not been processed (No at step S307), the controlling unit 39a returns the process to step S303 to cause the determining unit 51 to select one of the decomposition target materials. The controlling unit 39a performs the processing described above until all the decomposition target materials are determined to have been processed.

The following explains the processing of step S302. At step S302, the image reconstructing unit 36 generates the CT image by performing the reconstructing process using all or a part of the first data group obtained from the projection data storage unit 35. The reconstructing process using all the first data group mentioned above reconstructs an image representing a spatial distribution image of the CT value, for example, as in the case of the conventional X-ray CT apparatuses.

In the second embodiment, this operation is performed for the following reason. The image reconstruction taking the energy dependence of the X-ray absorption rate into account allows more accurate material decomposition to be performed than is performed by conventional image reconstruction based on integration that does not take the energy dependence into account. The image reconstruction taking the energy dependence into account requires, however, longer calculation time and larger computer resources than those required by the conventional image reconstruction. Accordingly, in the second embodiment, as a first stage, the decomposition target material is roughly discriminated following a simpler method using the CT value, and a determination is made as to whether a more detailed calculation is worth being performed. Only when the more detailed calculation is recognized to be worth being performed, the allocating process explained in the first embodiment is performed, and the image is reconstructed.

The expression that the image reconstructing unit 36 "performs the reconstructing process using a part of the first projection data group obtained from the projection data storage unit 35" means, for example, generating the spatial distribution image of the CT value by integrating the X-ray absorption rate calculated for each of the detector elements only with respect to a part of energy, and then using a reconstructing method, such as the FBP method. Specific examples of the part of energy mentioned above include, but are not limited to, an energy region selected as a region in which the intensity of the X-rays is higher. Data in energy regions in which the intensity of the X-rays is lower is not used, for example, for the following reason: The number of detected photons is not statistically sufficient, so that the signal-to-noise ratio is lower in such energy regions. Hence, the reconstruction is performed excluding the data with lower signal-to-noise ratios.

The processing of step S304 will be explained. At step S304, the determining unit 51 determines, based on the CT values of the CT image and the CT value corresponding to the decomposition target material, whether the decomposition target material is present in the imaging region. The expression "based on the CT values of the CT image and the CT value corresponding to the decomposition target material" means that the determination is made, for example, based on whether a value close to the CT value corresponding to the decomposition target material is present among the CT values of the CT image. Materials having similar properties exhibit roughly the same CT values, so that finding a rough CT value allows a rough estimation of what kind of material is present. Accordingly, the constituent material can be roughly estimated from the CT value. The CT value is, however, less suitable for material decomposition than, for example, the method utilizing the K absorption edge. For that reason, a subsequent stage process is performed using the second energy bins to allow the accurate material decomposition to be performed.

As described above, in the second embodiment, before the second data group is generated and used for the image reconstruction, the preliminary image reconstruction is used to determine whether the decomposition target material is present in the imaging region. This process can reduce the waiting time of the user when the decomposition target material is not present in the imaging region.

Third Embodiment

The following explains a third embodiment. In the second embodiment, the CT image is reconstructed with the simple method through the reconstructing process using all or a part of the first data group, and, based on the result of the reconstruction, the determination is made as to whether the second data group is to be generated and used to reconstruct the image for the decomposition target material. The third embodiment is the same as the second embodiment in that the image is preliminarily reconstructed with the simple method, and based on the result thereof, the determination is made as to whether the second data group is to be generated and used to reconstruct the image for the decomposition target material. However, the third embodiment uses a different simple method for reconstructing the image from the method of the second embodiment.

The determining unit 51 of the photon counting X-ray CT apparatus according to the third embodiment estimates an energy spectrum based on the first data group. Then, based on the estimated energy spectrum, the determining unit 51 determines whether the decomposition target material is present in the imaging region, and determines the second energy bins if the decomposition target material is present in the imaging region. If the determining unit 51 determines that the decomposition target material is present, the image reconstructing unit generates the image representing the distribution of the decomposition target material.

In the third embodiment, the process is performed following the same procedure as that of the second embodiment, except at steps S302 and S304.

In the third embodiment, at step S302, instead of step S302 in the second embodiment, the image reconstructing unit 36 estimates the energy spectrum based on the first data group.

When the determining unit 51 estimates the energy spectrum based on the first projection data group. The determining unit 51 may specifically estimate, for example, the energy dependence of a quantity corresponding to the absorption rate, that is, the energy spectrum, by converting the photon counting result for each energy level detected by corresponding one of the detector elements into the X-ray energy absorption rate, and simply summing the X-ray energy absorption rates for all the detecting elements 40. As another method, the determining unit 51 may estimate the energy spectrum by summing the quantities corresponding to the energy absorption rates for only certain detecting elements 40, that is, for example, for only detecting elements 40 having high signal strength, instead of summing the quantities corresponding to the energy absorption rates for all the detecting elements 40. As still another method, the determining unit 51 may estimate the energy spectrum in a simplified manner, for example, based on what is called a counting result at one view.

In the third embodiment, at step S304, instead of step S304 in the second embodiment, the determining unit 51 determines, based on the estimated energy spectrum, whether the decomposition target material is present in the imaging region (step S304). If the determining unit 51 determines that the decomposition target material is present in the imaging region (Yes at step S304), the same processing as that performed in the case of "Yes" at step S304 in the second embodiment is performed. If the determining unit 51 determines that the decomposition target material is not present in the imaging region (No at step S304), the same processing as that performed in the case of "No" at step S304 in the second embodiment is performed.

As an example of a method for the determining unit 51 to determine whether the decomposition target material is present in the imaging region, the determining unit 51 only needs to determine whether the energy spectrum estimated by the determining unit 51 behaves discontinuously as a function of the energy near the certain energy value unique to the decomposition target material. As a result, the determining unit 51 can determine whether the decomposition target material is present in the imaging region at a certain level of accuracy.

In this way, the third embodiment can further reduce the waiting time of the user when the decomposition target material is not present.

Fourth Embodiment

The following explains a fourth embodiment. In the fourth embodiment, an example of user input and output interfaces for receiving the designation of the decomposition target materials will be explained. In the fourth embodiment, the display unit 32 obtains a list of candidate materials for the decomposition target material, and displays for the user the list of candidate materials for the decomposition target material. The input unit 31 receives a selection or an input of names of decomposition target materials from the user who has referred to the display unit 32, and notifies the determining unit 51 of the received information.

Figure 11:
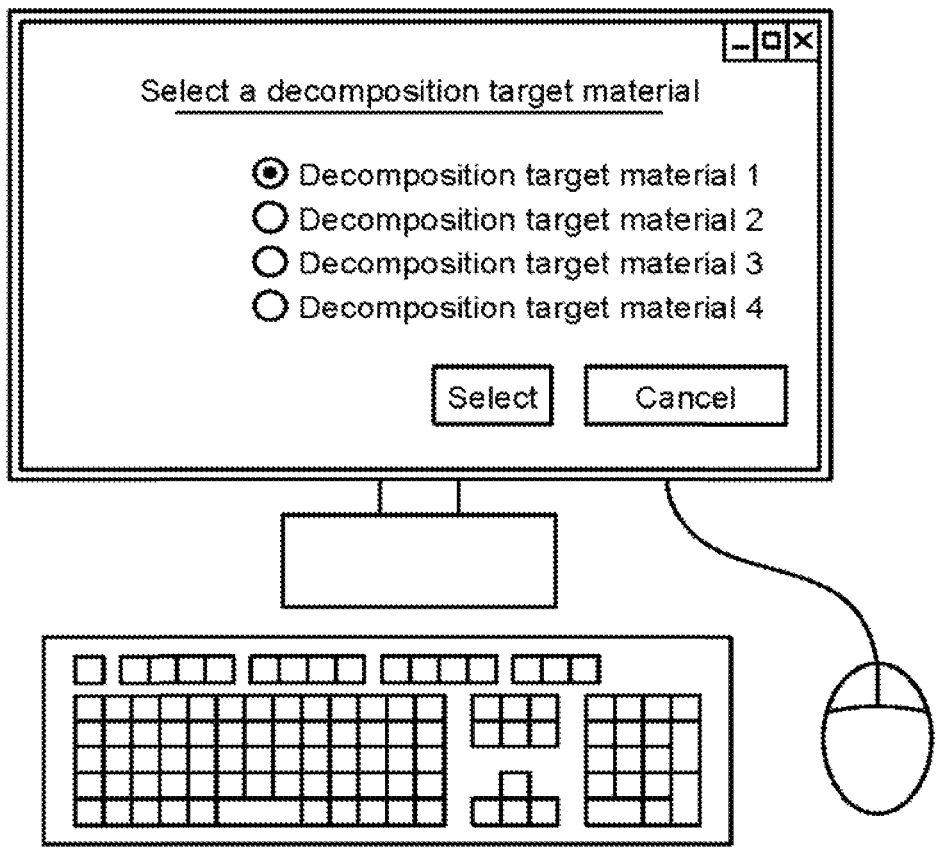
FIGS. 11 and 12 are drawings for explaining examples of user interfaces included in X-ray CT apparatuses according to a fourth embodiment and a fifth embodiment, respectively.

FIG. 11 is a drawing for explaining the example of the user interface included in an X-ray CT apparatus according to the fourth embodiment. A monitor serves as the display unit 32, which obtains the list of candidate materials for the decomposition target material from the database 38a and displays the obtained list for the user. A keyboard and a mouse serve as the input unit 31, which receives the selection or the input of the names of decomposition target materials from the user who has referred to the display unit 32. The input unit 31 detects a key input or a mouse operation by the user, and notifies the determining unit 51 of the detected information.

As a first example of a display mode, the display unit 32 displays the list of candidate materials for the decomposition target material on the monitor to notify the user of information. As a second example of the display mode, the display unit 32 uses a display device integrated with an input device, such as a tablet terminal, to notify the user of the information.

Examples of a method in which the input device receives the information from the user through the input unit 31 may include, but are not limited to, a method in which the keyboard is used as the input device to receive the key input from the user. The mouse may be used as the input device to receive the mouse input, such as a clicking or a drag-and-drop operation, from the user. The tablet terminal may be used as the input device to receive the input from the user who touches a button displayed on the tablet terminal. Hardware switches may be used as the input device to receive the input from the user who moves the hardware switches. For example, toggle switches or radio buttons may be used as the input device to receive the selection input from the user.

In this way, the photon counting X-ray CT apparatus according to the fourth embodiment can efficiently transmit the instruction of the user to the determining unit 51 by including the user input interface. Including the user output interface allows the user to check the content of the instruction to the determining unit 51 and the result of the output from the determining unit 51. As a result, convenience of the user can be improved.

Fifth Embodiment

The following explains a fifth embodiment. A photon counting X-ray CT apparatus according to the fifth embodiment includes, as the user input interface, input receiving components (such as the hardware switches) typified by keys of the keyboard, and uses them to receive the input of the information on the material of interest.

In the fifth embodiment, the input unit 31 includes at least one input receiving component associated with at least one candidate material for the decomposition target material, and receives the material associated with the input receiving component operated by the user as the decomposition target material. The input unit 31 notifies the determining unit 51 of the received information via the controlling unit 39a.

Figure 12:
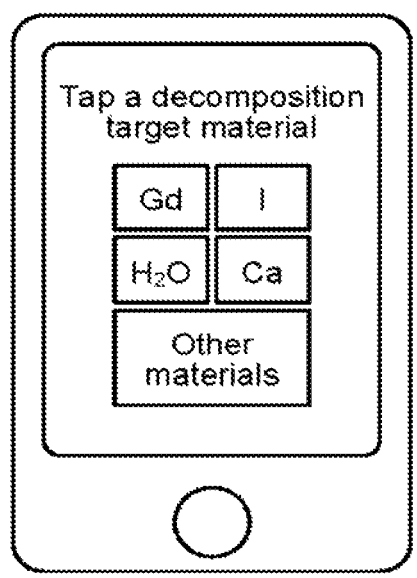

FIG. 12 is a drawing for explaining an example of the user interface included in the X-ray CT apparatus according to the fifth embodiment. A touch screen on the tablet terminal serves as the input unit 31, which receives the selection input of the decomposition target materials from the user. Buttons displayed as "Gd", "I", "$H_2O$", "Ca", and "Other materials" on the touch screen serve as the respective input receiving components. For example, "Gd" corresponds to a decomposition target material called "gadolinium", and "I" corresponds to a decomposition target material called "iodine". The tablet terminal notifies the determining unit 51 of the received information through a communication line.

As a first example of the input receiving components different from the above example, individual keys of the keyboard can be used. For example, the key "1" of the keyboard is associated with a decomposition target material A, and the key "2" of the keyboard is associated with a decomposition target material B. When the user presses a key of the keyboard associated with a decomposition target material, the input unit 31 receives the material associated with the key operated by the user as the information.

As a second example of the input receiving components, buttons displayed on a display screen can be used. For example, a "first button" displayed on the display screen is associated with the decomposition target material A, and a "second button" displayed on the display screen is associated with the decomposition target material B. When the user selects a button associated with a decomposition target material using the mouse, the input unit 31 receives the material associated with the button operated by the user as the information.

As a third example of the input receiving components, switches for controlling a current flowing in an electrical circuit, such as the toggle switches, can be used. For example, the decomposition target material A is selected when a switch is "on", and the decomposition target material is not selected when the switch is "off". When the user turns the switch "on", the input unit 31 receives the decomposition target material associated with the switch as the information.

In this way, the photon counting X-ray CT apparatus according to the fifth embodiment can improve the convenience of the user by including the input receiving components as the user input interface.

Sixth Embodiment

The following explains a sixth embodiment. The input unit 31 of a photon counting X-ray CT apparatus according to the sixth embodiment generates identifiers each combining one or more materials to be one or more decomposition target materials according to a request from the user, and causes the display unit 32 to display information on the identifiers. The input unit 31 then receives information from the user who has referred to the display unit 32. As an example of an aspect of the present embodiment, the input unit 31 generates, as selection buttons, the identifiers each combining one or more materials to be one or more decomposition target materials according to the request from the user, and allows the user to select the decomposition target material or materials associated with one of the selection buttons so as to allow the user to easily select a material or materials of interest frequently used.

The "identifier combining one or more materials to be one or more decomposition target materials according to the request from the user" mentioned above represents, for example, an identifier called "first setting" associated with three variables, that is, a "first decomposition target material name", a "second decomposition target material name", and a "third decomposition target material name".

In other words, the identifier called "first setting" is associated with a situation in which the value of the first decomposition target material name is a predetermined value, the value of the second decomposition target material name is another predetermined value, and the value of the third decomposition target material name is still another predetermined value. The value of the first decomposition target material name may be, for example, a character string value of "Gd", or a numerical value of "1". The variables may be logical values as needed.

Where needed, the input unit 31 causes the display unit 32 via the controlling unit 39a to display the information on the identifier combining one or more materials according to the request from the user. For example, the display unit 32 displays information indicating that the identifier "first setting" is associated with the variables of the "first decomposition target material", the "second decomposition target material", and the "third decomposition target material". The display unit 32 also displays information indicating that the value of the "first decomposition target material" is the predetermined value, the value of the "second decomposition target material" is the other predetermined value, and the value of the "third decomposition target material" is the still other predetermined value.

After the information on the identifiers is displayed on the display unit 32, the input unit 31 receives the information from the user. For example, if the user aligns the cursor with a button labeled as "Register first setting as photographing parameter" and depresses a mouse button, the input unit 31 receives the information associated with the identifier "first setting" as a photographing parameter. Specifically, the input unit 31 interprets what kind of information is associated with the identifier "first setting", and notifies the controlling unit 39a of the information indicating that a total of three decomposition target materials are included and the predetermined values of the "first decomposition target material", the "second decomposition target material", and the "third decomposition target material". The values of the variables obtained by the controlling unit 39a are transmitted to the determining unit 51. The input unit 31 may receive a change in the decomposition target material from the user.

As a modification of the sixth embodiment, decomposition target materials frequently used by the user may be arranged so as to be easily identifiable on the display screen so that the user can easily select the frequently used decomposition target material. As a first example, identifiers associated with the decomposition target material frequently used by the user may be easily identifiably displayed on the display device. As a second example, such identifiers may be displayed in highly visible positions on the display device. As a third example, identifiers each combining one or more decomposition target materials frequently used by the user may be displayed in a highly visible color or in highly visible positions on the display device. As a fourth example, the identifiers associated with the decomposition target material or the identifiers each combining one or more of the decomposition target materials, which are frequently used by the user, may be initially set as default values.

In this way, the photon counting X-ray CT apparatus according to the sixth embodiment generates the identifiers each combining one or more materials to be one or more decomposition target materials according to the request from the user, and displays the information on the identifiers on the display device. If the user who has referred to the display device selects one of the identifiers, the information on the corresponding decomposition target material is transmitted to the determining unit 51. As a result, the user need not enter information on each of the decomposition target materials, so that the convenience of the user can be improved.

Seventh Embodiment

The following explains a seventh embodiment. The determining unit 51 of a photon counting X-ray CT apparatus according to the seventh embodiment is configured to be capable of automatically setting the decomposition target material without requiring the user to set them. In other words, as an example, the determining unit 51 selects, by default, the decomposition target material that the user always wants to select. As another example, the determining unit 51 is configured to be capable of automatically setting the decomposition target material according to the frequency of use thereof.

In the seventh embodiment, the determining unit 51 automatically selects candidates for the decomposition target material without requiring the user to enter the decomposition target material each time a photograph is taken. Specifically, based on data in which imaging condition for photographing performed in the past are associated with material selected as decomposition target material under the imaging condition, the determining unit 51 of the photon counting X-ray CT apparatus according to the seventh embodiment estimates material that meet the imaging condition for photographing currently performed, and determines the second energy bins, assuming the estimated material as the decomposition target material.

The imaging condition for photographing performed in the past refer to, for example, the type of contrast agent used, the organ of a photographed subject, the sex, age, body height, body weight, and disease name of the subject, the photographing time, the patient ID, the name of a doctor providing treatment, and the name of a hospital. In the seventh embodiment, each time a photograph is taken, the controlling unit 39a obtains the imaging condition at that time, and notifies the database 38a of the imaging condition. After the determining unit 51 determines the decomposition target material, the controlling unit 39a obtains the information on the decomposition target material from the determining unit 51, and notifies the database 38a of the information on the decomposition target material.

The database 38a stores the conditions on the imaging condition obtained via the controlling unit 39a and the information on the decomposition target material selected by the determining unit 51 when the photograph was taken in a manner associated with each other. Based on the imaging condition and the information on the selected decomposition target material stored in a manner associated with the imaging condition, the determining unit 51 estimates the material that meet the imaging condition for the photographing, and assumes the estimated material as the decomposition target material.

As a first example of a method for the estimation, the determining unit 51 selects frequently used decomposition target material as the decomposition target material. As a second example of the method for the estimation, the determining unit 51 selects the decomposition target material based on the information on the type of the contrast agent used. As a third example of the method for the estimation, the determining unit 51 selects the decomposition target material based on the information on the disease name. As a fourth example of the method for the estimation, the determining unit 51 selects, as the decomposition target material, decomposition target material frequently selected in the past by the doctor providing treatment to the patient photographed. As a fifth example of the method for the estimation, the determining unit 51 automatically selects, as the decomposition target material, elements contained in the contrast agent used.

After determining the decomposition target material in this way, the determining unit 51 follows the procedure described in the first embodiment to determine the second energy bins. After determining the second energy bins, the determining unit 51 notifies the allocating unit 52 of the information on the second energy bins. The allocating unit 52 generates the second data group, and the image reconstructing unit 36 performs the image reconstruction based on the generated second data group.

As described above, in the seventh embodiment, the determining unit 51 estimates the candidates for the decomposition target material and presets the material of interest based thereon without requiring the user to enter the decomposition target material each time the imaging is performed. The decomposition target material is automatically selected without requiring the user to enter parameters one by one, so that the convenience of the user can be improved.

As a modification of the seventh embodiment, the determining unit 51 uses, as the method for the estimation, the method for estimating the material based on the data in which imaging condition for photographing performed in the past are associated with material selected as decomposition target material under the imaging condition, and receives an input of "decomposition target material to be always selected" from the user via the input unit 31. The determining unit 51 selects material as the decomposition target material, based on the data and the input from the user.

The determining unit 51 may use, as the method for the estimation, a method in which the past data is not used and the decomposition target material is selected based on only the "decomposition target material to be always selected" received as the input from the user.

Eighth Embodiment

The following explains an eighth embodiment. In the embodiments described above, the database 38a holds the certain energy values unique to the decomposition target material. If, however, the decomposition target material is molecules or mixtures, the database 38a cannot necessarily hold the certain energy values unique to all the decomposition target material. Even in such cases, the determining unit 51 of a photon counting X-ray CT apparatus according to the eighth embodiment calculates the energy value unique to a decomposition target material. Specifically, the photon counting X-ray CT apparatus according to the eighth embodiment uses a value calculated based on the composition of the decomposition target material as the energy value unique to the decomposition target material.

As a first example of a method for the calculation, a method for calculating an energy value unique to a molecule or a constituent material consisting of a plurality of materials is used in which the energy value unique to the decomposition target material is calculated from the composition ratio or the weight ratio between elements. As a second example of the method for the calculation, if the decomposition target material is a mixture of a known material and a small amount of impurities, a value proportional to the amount of the mixed impurities obtained by multiplying the amount of the mixed impurities by a proportionality constant is added to the energy value unique to the known material so as to estimate the energy value unique to the decomposition target material.

As an example of a situation in which the eighth embodiment is applicable, the material decomposition is applied to a metal, particularly an alloy, implanted in the subject. The metal scatters the X-rays to cause what are called metal artifacts. The material decomposition can be accomplished by estimating the energy value unique to the metal, particularly to the alloy. As a result, the contribution of the metal artifacts can be properly subtracted from the generated image of the subject.

As described above, in the eighth embodiment, the determining unit 51 calculates the certain energy value unique to the decomposition target material based on the composition of the decomposition target material. This calculation allows the decomposition target material to be estimated even if the database 38a does not include the energy value unique to the decomposition target material.

In the first to eighth embodiments described above, the case has been explained in which the allocating unit 52 generates the second projection data group as the second data group by allocating the first projection data group generated from the first data group by the pre-processing unit 34. In the first to eighth embodiments, however, the allocating unit 52 may allocate the first data group to generate the second data group, and the pre-processing unit 34 may generate the second projection data group from the second data group. In such a case, the allocating unit 52 may be provided at the previous stage of the pre-processing unit 34 in the image processing apparatus 30a, or at the subsequent stage of the data acquiring unit 14a in the gantry device 10a. In the first to eighth embodiments, the example has been explained in which the determining unit 51 uses the grouping procedure through which the certain energy values unique to the decomposition target material that is material to be discriminated substantially coincide with the boundaries between the adjacent second energy bins. However, as an example of the grouping procedure, a grouping procedure may be employed through which the certain energy values unique to the decomposition target material do not coincide with the boundaries of the generated second energy bins. For example, a grouping procedure may be employed through which one interval of the second energy bins coincides with an interval starting near the upper end of the K absorption edge, and another interval of the second energy bins coincides with an interval starting near the lower end of the K absorption edge. For example, the example has been explained with reference to FIG. 6, in which the energy bins E101, E102, E103, and E104 are determined to be the second energy bins; however, instead of the energy bin E102, an interval obtained by bundling together the energy bins E4 and E5 may be determined to be one of the second energy bins, and, instead of the energy bin E103, an interval obtained by bundling together the energy bins E8 and E9 may be determined to be another of the second energy bins. In such a case, the data is avoided being obtained from exactly the K absorption edge where the signal strength greatly changes, so that data surely on the low-energy side of the K absorption edge and data surely on the high-energy side of the K absorption edge can be obtained. In other words, in the example described above, the second energy bins capable of discriminating the decomposition target material can be determined even if the measured value of the K absorption edge of the decomposition target material fluctuates from the ideal value. As a result, in the example described above, the image can be obtained that can surely decompose the decomposition target material. Alternatively, for example, a grouping procedure may be employed through which the energy bins are grouped so that one interval of the second energy bins and another interval of the second energy bins contain roughly the same "total amount of noise". In such a case, the energy bins have roughly the same level of error, so that the error contained in the final output image can be reduced.

The photon counting imaging method explained in the first to eighth embodiments may be carried out by an image processing apparatus provided independently of the photon counting X-ray CT apparatus. Such an image processing apparatus can carry out the photon counting imaging method explained in the first to eighth embodiments, by obtaining the first data group from the photon counting X-ray CT apparatus.

Ninth Embodiment

Figure 13:
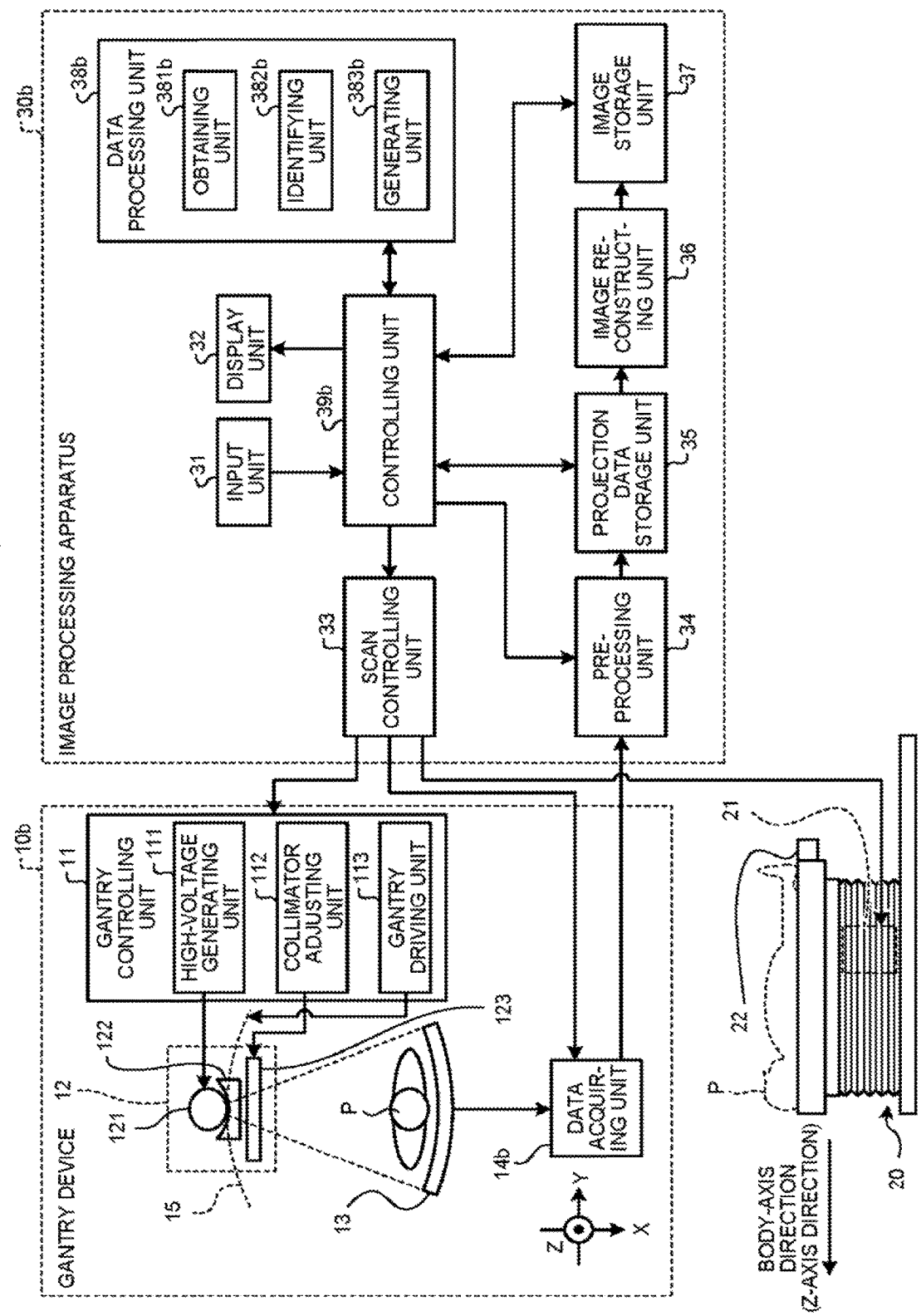
FIG. 13 is a diagram of a configuration of a photon counting X-ray CT apparatus according to the first embodiment.

First, with reference to FIG. 13, a configuration of a photon counting X-ray CT apparatus 1*b* according to a ninth embodiment will be explained. FIG. 13 is a diagram of the configuration of the photon counting X-ray CT apparatus 1*b* according to the ninth embodiment. As illustrated in FIG. 13, the photon counting X-ray CT apparatus 1*b* includes a gantry device 10*b*, the couch device 20, and an image processing apparatus 30*b*. The photon counting X-ray CT apparatus 1*b* is an apparatus capable of performing the photon counting CT imaging. The configuration of the photon counting X-ray CT apparatus 1*b* according to the ninth embodiment is not limited to the following configuration. In the following explanation, explanation of the configurations described above will be omitted where appropriate.

The gantry device 10*b* irradiates the subject P with the X-rays, and acquires projection data (to be explained later). The gantry device 10*b* includes the gantry controlling unit 11, the X-ray generating device 12, the detector 13, a data acquiring unit 14*b*, and the rotating frame 15.

The detector 13 includes the detecting elements that outputs signals according to the incident X-rays. Specifically, the detector 13 is a multi-row detector including the detecting elements in the channel direction and the slice direction. The channel direction corresponds to the circumferential direction of the rotating frame 15, and the slice direction corresponds to the body-axis direction of the subject P. Each of the detecting elements included in the detector 13 outputs a pulsed electric signal each time a photon of an X-ray is incident so that the energy of photons can be measured and the number of photons can be counted. The data acquiring unit 14*b* (to be explained later) can count the number of the photons incident into each of the detecting elements by counting the number of the electric signals. The data acquiring unit 14*b* (to be explained later) can measure the energy of the photons that have caused the output of the electric signals, by performing the calculating process based on the waveform of each of the pulses.

The detecting elements included in the detector 13 are cadmium-telluride (CdTe)-based semiconductor devices. The detector 13 is what is called a direct-conversion-type detector. The direct-conversion-type detector refers to a detector that converts the photons incident into the detecting elements into the electric signals. The electric signals are output from the detector 13 by at least one of the following mechanisms: one is that electrons generated by the incidence of the photons run toward a collector electrode having a positive potential, and the other is that holes generated by the incidence of the photons run toward a collector electrode having a negative potential. The detector 13 illustrated in FIG. 13 may be what is called an indirect-conversion-type detector. The indirect-conversion-type detector refers to a detector that uses the scintillators to convert the photons incident into the detecting elements into scintillator light, and uses the photodetectors, such as the photomultiplier tubes, to convert the scintillator light into the electric signals.

The data acquiring unit 14*b* acquires count information that is a result of the counting process using the electric signals output from the detector 13. The count information is information in which the count value of the photons, the position of the X-ray tube 121, the positions of the detecting elements receiving the incident photons, and the energy of the photons are associated with one another. The position of the X-ray tube 121 is called a view. Moreover, the data acquiring unit 14*b* generates the projection data of each of the energy bins having a predetermined width by allocating the count value of the photons to the energy bins set in advance according to each value of the energy of the photons measured from the electric signals. The luminance value of each point of the projection data represents the number of photons. The count value of the photons included in the count information may be a value per unit time. The count value of the photons per unit time is called a count rate. The image processing apparatus 30*b* may perform the process to allocate the count value of the photons to the energy bins set in advance.

Figure 14:
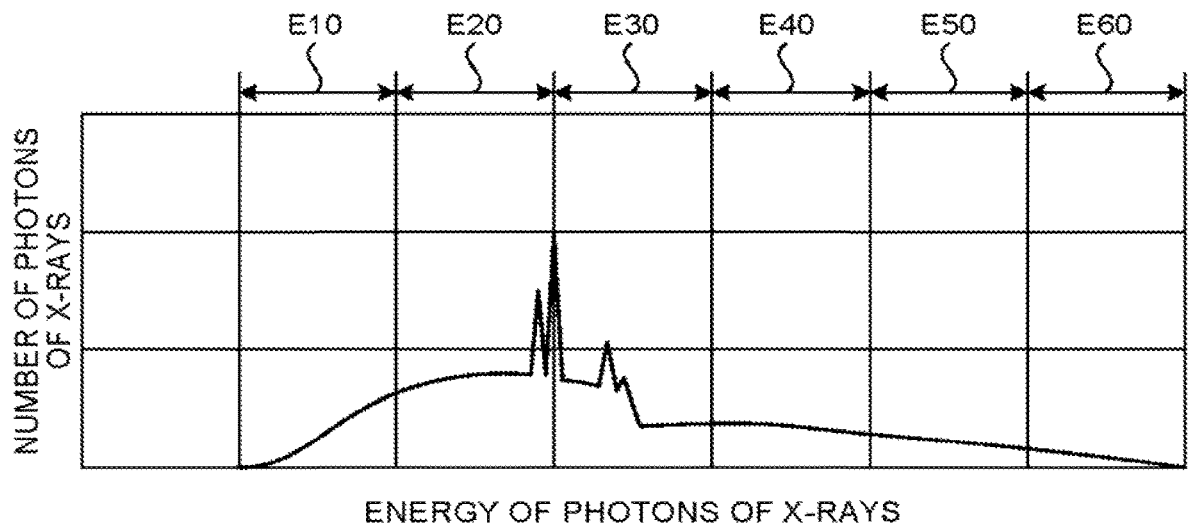
FIG. 14 is a diagram of a plurality of energy bins used in the first embodiment.

FIG. 14 is a diagram of the energy bins used in the ninth embodiment. For example, as illustrated in FIG. 14, the photon counting X-ray CT apparatus 1*b* can set energy bins E10, E20, E30, E40, E50, and E60 having the same energy width along the energy distribution of the X-rays emitted from the X-ray tube 121. The data acquiring unit 14*b* or the image processing apparatus 30*b* sets the energy bins.

For example, the data acquiring unit 14*b* classifies the count value of the photons acquired by the respective detecting elements for each position of the X-ray tube 121 for each value of the energy of the photons, and allocates the count value to any one of the energy bins E10, E20, E30, E40, E50, and E60 illustrated in FIG. 14. As a result, the data acquiring unit 14*b* generates the projection data of the energy bins E10, E20, E30, E40, E50, and E60.

The method for setting the energy bins along the energy distribution of the X-rays emitted from the X-ray tube 121 is not limited to that illustrated in FIG. 14. For example, the number and width of the energy bins can be set to any values. The energy bins may partially overlap one another. Moreover, the photon counting X-ray CT apparatus 1*b* according to the ninth embodiment may be configured to allow the user to freely change the setting of the energy bins. For example, a controlling unit 39*b* (to be explained later) notifies the gantry device 10*b* of the setting information of the energy bins so as to control the allocation of the count value of the photons performed by the data acquiring unit 14*b*.

The data acquiring unit 14*b* transmits the acquired projection data of the energy bins to the image processing apparatus 30*b*. For example, the data acquiring unit 14*b* integrates the projection data for each position of the X-ray tube 121 into a sinogram data format, and transmits the result. The sinogram refers to data obtained by arranging the signals detected by the detector 13 for each position of the X-ray tube 121. The sinogram is data obtained by assigning the signals detected by the detector 13 to a two-dimensional orthogonal coordinate system having the axes in the view direction from the position of the X-ray tube 121 and in the channel direction described above. The data acquiring unit 14*b* generates the sinogram row by row in the slice direction. The following explanation exemplifies a case in which the projection data is a sinogram. The data acquiring unit 14*b* is also called a data acquisition system (DAS).

The couch device 20 includes the couch driving device 21 and couchtop 22, on which the subject P is placed. Under the control of the scan controlling unit 33 (to be explained later), the couch driving device 21 moves the subject P in the rotating frame 15 by moving, in the Z-axis direction, the couchtop 22 on which the subject P is placed. The gantry device 10*b* can perform the same scan as that performed by the gantry device 10*a*.

The image processing apparatus 30*b* includes the input unit 31, the display unit 32, the scan controlling unit 33, the pre-processing unit 34, the projection data storage unit 35, the image reconstructing unit 36, the image storage unit 37, a data processing unit 38*b*, and the controlling unit 39*b*.

Under the control of the controlling unit 39*b*, the scan controlling unit 33 performs the same control as that of the scan controlling unit 33 according to the first embodiment.

The pre-processing unit 34 applies correcting processes, such as the logarithmic transformation, the offset correction, the sensitivity correction, the beam hardening correction, and a scattered radiation correction, to the projection data generated by the data acquiring unit 14*b*, and stores the result in the projection data storage unit 35. The projection data that has been subjected to the correcting processes by the pre-processing unit 34 is also called raw data.

The projection data storage unit 35 stores the raw data, that is, the projection data that has been subjected to the correcting processes by the pre-processing unit 34. The image reconstructing unit 36 reconstructs the projection data stored in the projection data storage unit 35 to generate reconstructed images. Examples of various methods for reconstruction include, but are not limited to, a back-projection process. Examples of the back-projection process include, but are not limited to, a filtered back projection (FBP) method. The image reconstructing unit 36 may use, for example, a successive approximation method to perform the reconstructing process. The image reconstructing unit 36 stores the generated reconstructed images in the image storage unit 37.

Each of the projection data storage unit 35 and the image storage unit 37 described above can be implemented, for example, in a semiconductor memory device such as a random access memory (RAM) or a flash memory, a hard disk, or an optical disc. Each of the scan controlling unit 33, the pre-processing unit 34, the image reconstructing unit 36, and the controlling unit 39*b* can be implemented as an integrated circuit, such as an application specific integrated circuit (ASIC) or a field programmable gate array (FPGA), or as an electronic circuit, such as a central processing unit (CPU) or a microprocessing unit (MPU).

The data processing unit 38*b* includes an obtaining unit 381*b*, an identifying unit 382*b*, and a generating unit 383*b*. The obtaining unit 381*b* obtains information on target material to be discriminated among materials that can be present in a predetermined region in the subject P from which the projection data of the energy bin set on the energy distribution of the X-rays emitted from the X-ray tube 121 has been acquired. The information on the target material to be discriminated obtained by the obtaining unit 381*b* includes the target materials of the material decomposition selected by the user. The identifying unit 382*b* identifies energy bins to be used for material decomposition among the energy bins. The generating unit 383*b* performs the material decomposition using the projection data of the energy bins identified by the identifying unit 382*b*, and generates an image for displaying the result of the material decomposition.

The controlling unit 39*b* controls the photon counting X-ray CT apparatus 1*b* by controlling the operations of the gantry device 10*b*, the couch device 20, and the image processing apparatus 30*b*. The controlling unit 39*b* controls the scan controlling unit 33 to perform the scan, and acquires the projection data from the gantry device 10*b*. The controlling unit 39*b* controls the pre-processing unit 34 to apply the above-mentioned correcting process to the projection data. The controlling unit 39*b* controls the display unit 32 to display the projection data stored in the projection data storage unit 35 and the images stored in the image storage unit 37. The controlling unit 39*b* controls the data processing unit 38*b* to perform the material decomposition.

Figure 15:
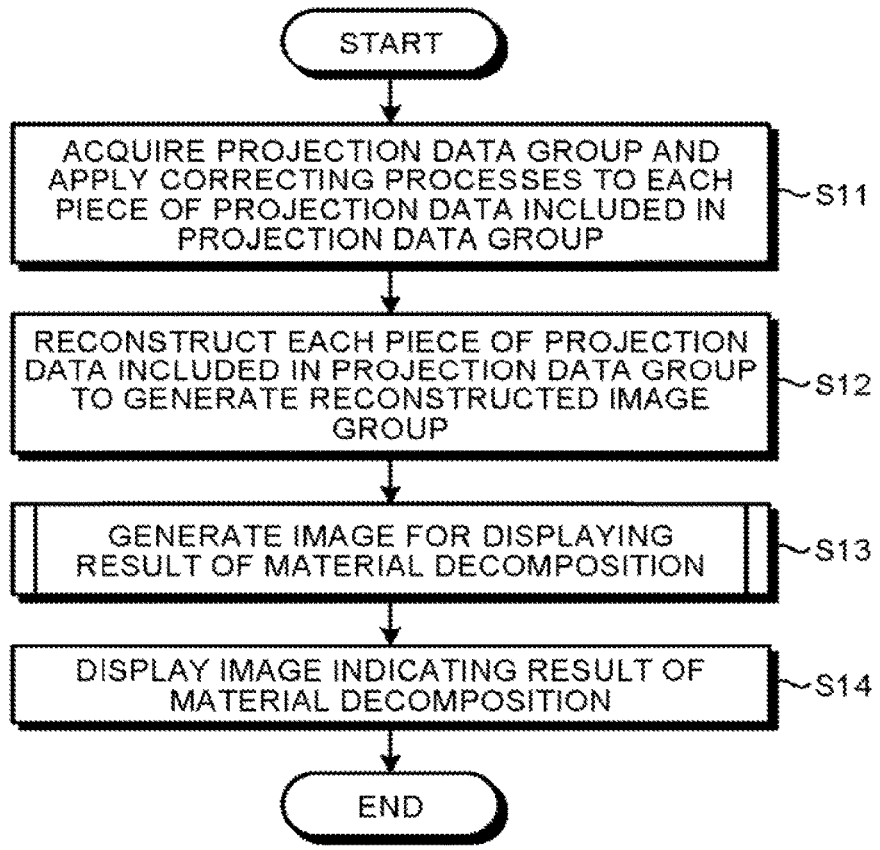
FIG. 15 is a flowchart of a procedure of material decomposition performed by the photon counting X-ray CT apparatus according to the first embodiment.
Figure 16:
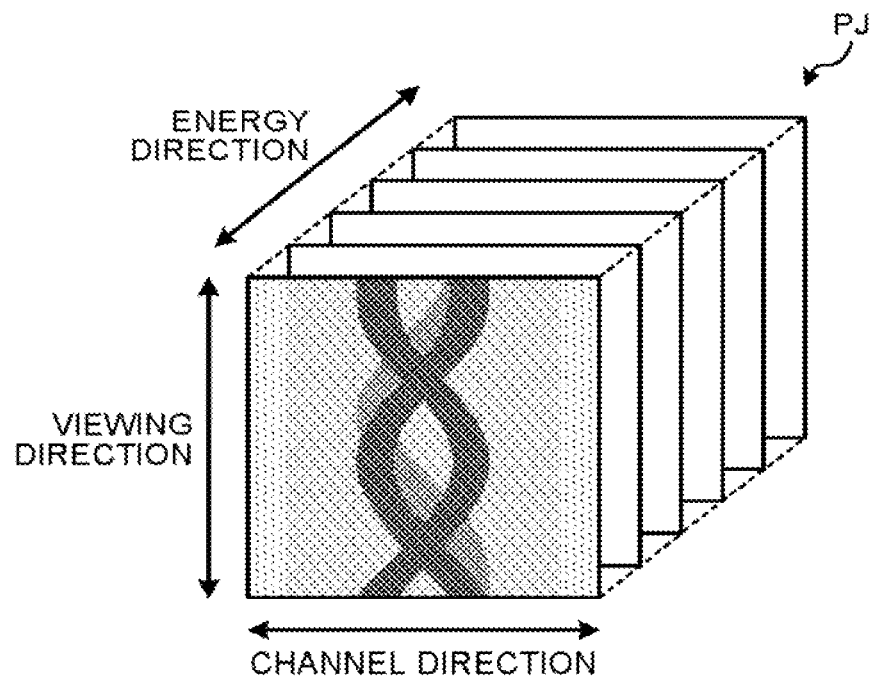
FIG. 16 is a drawing of an example of a projection data group in the first embodiment.
Figure 17:
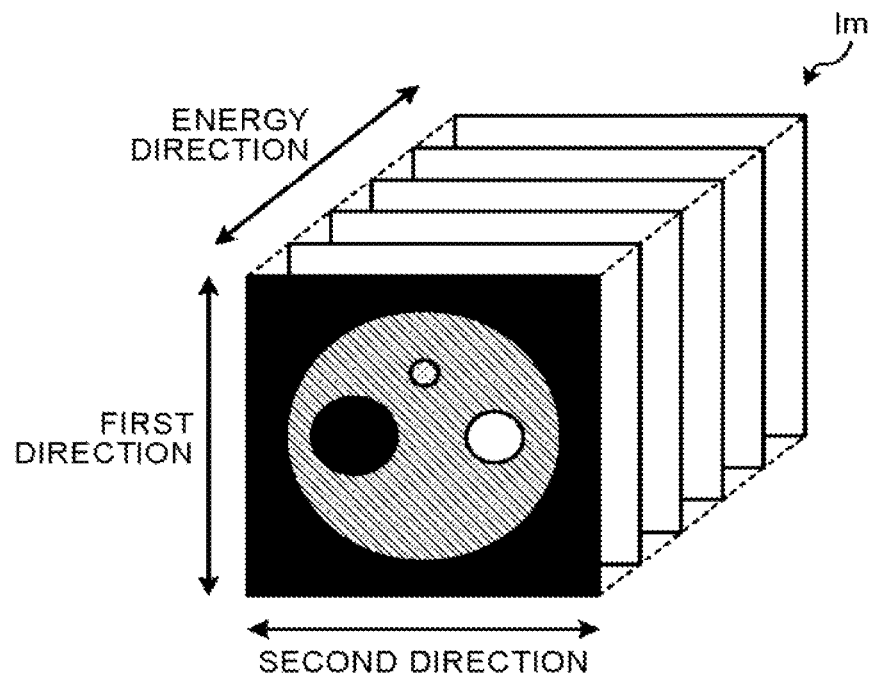
FIG. 17 is a drawing of an example of a reconstructed image group in the first embodiment.
Figure 18:
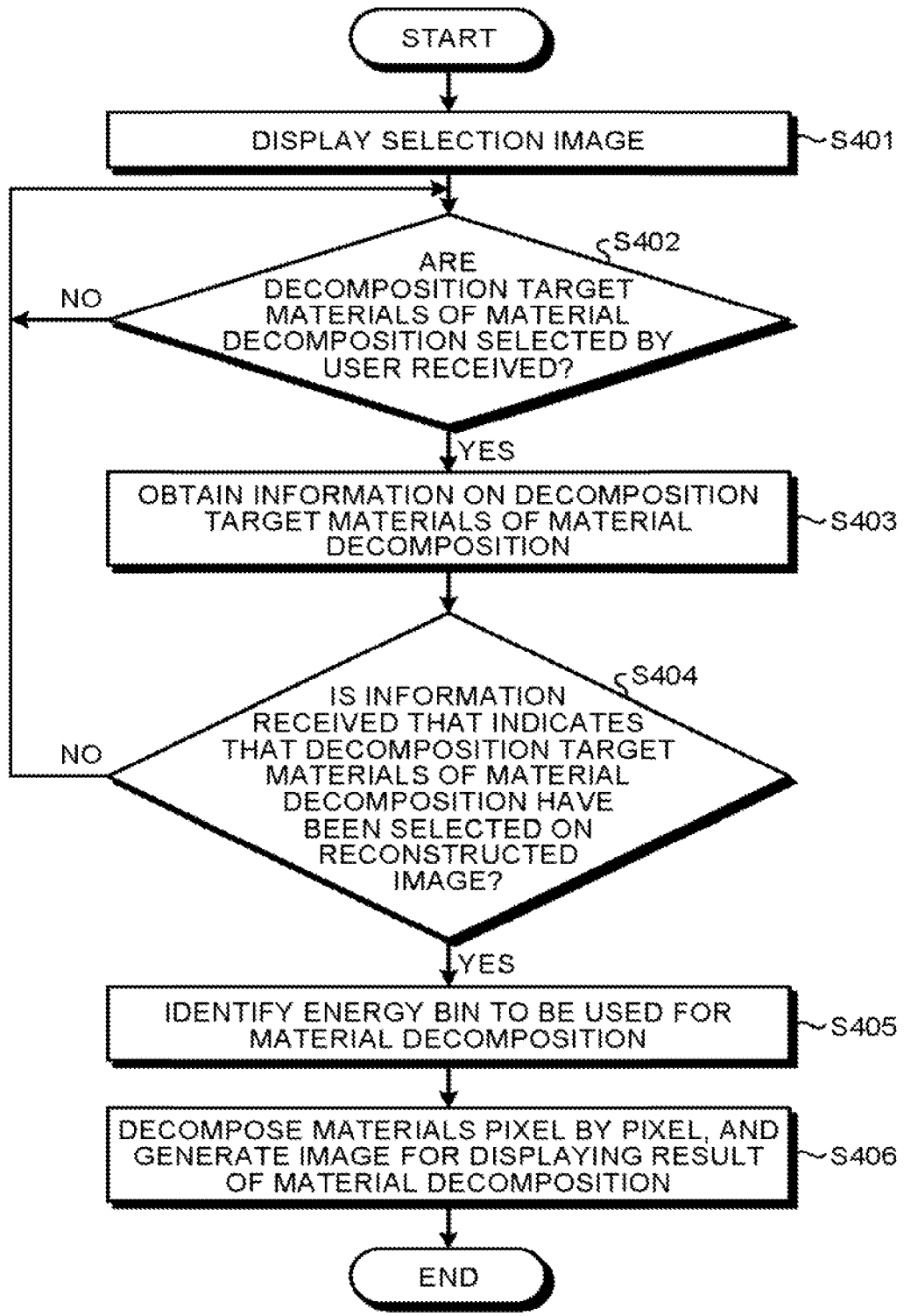
FIG. 18 is a flowchart of a procedure carried out at step S13 of FIG. 15 in the first embodiment.
Figure 19:
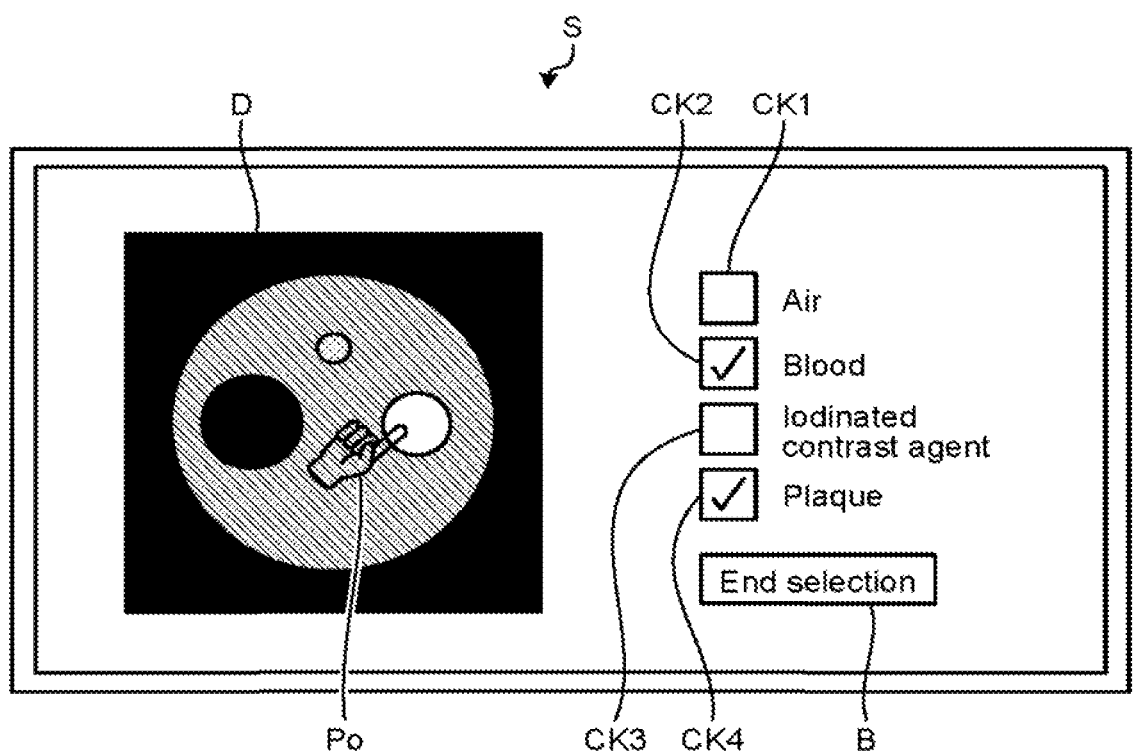
FIG. 19 is a drawing of an example of a selection image in the first embodiment.

The following explains the material decomposition performed by the data processing unit 38*b*, with reference to FIGS. 15 to 19. FIG. 15 is a flowchart of a procedure of the material decomposition performed by the photon counting X-ray CT apparatus 1*b* according to the ninth embodiment. FIG. 16 is a drawing of an example of the projection data group in the ninth embodiment. FIG. 17 is a drawing of an example of the reconstructed images in the ninth embodiment. FIG. 18 is a flowchart of a procedure carried out at step S13 of FIG. 15. FIG. 19 is a drawing of an example of a selection image in the ninth embodiment.

As illustrated in FIG. 15, the controlling unit 39*b* controls the gantry device 10*b*, the couch device 20, and the image processing apparatus 30*b* to perform the photon counting CT scan so as to acquire the projection data group, and controls the pre-processing unit 34 to apply the above-mentioned correcting process to each piece of the projection data included in the projection data group (step S11). As illustrated in FIG. 16, a projection data group PJ includes the projection data of the energy bins. Specifically, the projection data group PJ includes the projection data of the energy bins E10, E20, E30, E40, E50, and E60 illustrated in FIG. 14. In the projection data of each of the energy bins, the vertical direction corresponds to the view direction, and the horizontal direction corresponds to the channel direction, as illustrated in FIG. 16. In FIG. 16, the pieces of the projection data of the energy bins are illustrated being arranged in the energy direction with the view directions and the channel directions aligned with one another. The acquired projection data group PJ is stored in the projection data storage unit 35.

As illustrated in FIG. 15, the image reconstructing unit 36 reconstructs each piece of the projection data included in the projection data group PJ stored in the projection data storage unit 35 to generate a reconstructed image group Im illustrated in FIG. 17 (step S12). As illustrated in FIG. 17, the reconstructed image group Im includes the reconstructed images of the energy bins. Specifically, the reconstructed image group Im includes the reconstructed images of the energy bins E10, E20, E30, E40, E50, and E60 illustrated in FIG. 14. As illustrated in FIG. 17, the reconstructed images of the energy bins are data obtained by assigning, for example, the linear attenuation coefficient and the CT value to the two-dimensional orthogonal coordinate system having the axes in a first direction and a second direction orthogonal to the first direction. In other words, the luminance values of respective pixels of the reconstructed images represent, for example, the linear attenuation coefficient and the CT value. In FIG. 17, the reconstructed images of the energy bins are illustrated being arranged in the energy direction with the first and second directions aligned with one another. The generated reconstructed image group Im is stored in the image storage unit 37.

As illustrated in FIG. 15, the controlling unit 39b controls the data processing unit 38b to perform the material decomposition, and generates the image for displaying the result of the material decomposition (step S13). The image for displaying the result of the material decomposition refers to data for displaying the image for displaying information on the target material of the material decomposition. The information on the target material of the material decomposition includes, for example, types, amounts, and densities of the material. The display unit 32 receives the image, and displays the image indicating the result of the material decomposition (step S14). The following explains the details of step S13.

As illustrated in FIG. 18, the display unit 32 displays a selection image S illustrated in FIG. 19 (step S401). As illustrated in FIG. 19, the selection image S includes a pointer Po, a display area D, a button B, and checkboxes CK1, CK2, CK3, and CK4 displayed in conjunction with material that can be present in the predetermined region in the subject P from which the projection data of the energy bins has been acquired. The material that can be present in the predetermined region in the subject P from which the projection data of the energy bins has been acquired refers to the candidates for target of the material decomposition. The candidates for the material decomposition displayed in the selection image S are set in advance, and the number of the candidates is not limited.

As illustrated in FIG. 19, the selection image S includes the display area D in which a reconstructed image derived from the projection data of the energy bins is displayed. For example, a total energy reconstructed image is displayed in the display area D. The total energy reconstructed image is a reconstructed image obtained by summing up the luminance values of the respective pixels of all the reconstructed images included in the reconstructed image group Im. The image displayed in the display area D is not limited to the total energy reconstructed image. For example, the controlling unit 39b may cause the display unit 32 to display a reconstructed image obtained by reconstructing projection data obtained by summing up the count values of photons of pixels in at least two pieces of the projection data among the pieces of the projection data corresponding to the energy bins E10, E20, E30, E40, E50, and E60. The controlling unit 39b may cause the display unit 32 to display a total energy reconstructed image acquired in the past with a large dose of X-rays.

The target materials of the material decomposition refer to materials or tissues, for each of which the linear attenuation coefficient and the energy dependence thereof are known. The items displayed with the checkboxes are not limited to the materials or the tissues. For example, the name of an organ or a disease may be displayed with a checkbox in the selection image, and selecting the organ or the disease may display candidates for the target materials of the material decomposition related to the selected organ or disease in conjunction with the checkbox.

As illustrated in FIG. 18, the controlling unit 39b determines whether the target materials of the material decomposition selected by the user using the selection image S are received at a pixel corresponding to the point at which the material decomposition is performed (step S402).

The user first uses the pointer Po to select the pixel corresponding to the point at which the material decomposition is performed, in the total energy reconstructed image displayed in the display area D. The user then uses the checkboxes CK1, CK2, CK3, and CK4 illustrated in FIG. 19 to select the target materials of the material decomposition. The user can include air among the target materials of the material decomposition by checking the checkbox CK1. The user can include blood among the target materials of the material decomposition by checking the checkbox CK2. The user can include an iodinated contrast agent among the target materials of the material decomposition by checking the checkbox CK3. The user can include plaque among the target materials of the material decomposition by checking the checkbox CK4.

If the controlling unit 39b has received the target materials of the material decomposition selected by the user using the selection image S at the pixel corresponding to the point at which the material decomposition is performed (Yes at step S402), the process goes to step S403. If the controlling unit 39b has not received the target materials of the material decomposition selected by the user using the selection image S at the pixel corresponding to the point at which the material decomposition is performed (No at step S402), the process returns to step S402.

As illustrated in FIG. 18, the obtaining unit 381b obtains the information on the target materials of the material decomposition selected by the user at step S402 (step S403). Materials or tissues that the obtaining unit 381b does not obtain are deemed to be not present at the point at which the material decomposition is performed represented by the pixel selected by the user using the pointer Po.

As illustrated in FIG. 18, the obtaining unit 381b determines whether information is received indicating that the target materials of the material decomposition have been selected on the reconstructed image displayed in the display area D (step S404). If the target materials of the material decomposition have been selected, the user depresses the button B using the pointer Po to enter the information indicating that the target materials of the material decomposition have been selected. In other words, the obtaining unit 381b determines whether the user has entered the information indicating that the target materials of the material decomposition have been selected on the reconstructed image displayed in the display area D. If the obtaining unit 381b has not received the information indicating that the target materials of the material decomposition have been selected on the reconstructed image displayed in the display area D (No at step S404), the process returns to step S402. If the obtaining unit 381b has received the information indicating that the target materials of the material decomposition have been selected on the reconstructed image displayed in the display area D (Yes at step S404), the process goes to step S405.

The obtaining unit 381b may obtain the information on the target materials of the material decomposition at a plurality of pixels selected in a batch on the reconstructed image displayed in the display area D. Examples of the method for selecting the pixels in a batch on the reconstructed image displayed in the display area D include, but are not limited to, a method in which a region including the pixels selected by the user is extracted by a region growing method using threshold processing, and pixels in the extracted region are selected, and a method in which pixels in a region set by the user using a drawing tool are selected. The user may select all pixels on the reconstructed image displayed in the display area D in a batch.

As illustrated in FIG. 18, the identifying unit 382b identifies energy bins to be used for the material decomposition among the energy bins set along the energy distribution of the X-rays emitted from the X-ray tube 121 (step S405). In general, increasing the energy of the X-rays improves the accuracy of the energy and the count value of the photons included in the count information acquired by the detector 13. Accordingly, the identifying unit 382b identifies, as energy bins to be used for the material decomposition among the energy bins, a smaller number of energy bins than the total number of the energy bins, in the descending order of the energy. The identifying unit 382b may alternatively identify, as energy bins to be used for the material decomposition among the energy bins, energy bins that do not overlap the K absorption edge of the decomposition target material. The value of the linear attenuation coefficient greatly varies between both sides of the K absorption edge, so that the independence of two expressions included in Expression (2) (to be explained later) increases. As a result, the process performed by the identifying unit 382b allows the data processing unit 38b to accurately perform the material decomposition.

As illustrated in FIG. 18, the generating unit 383b decomposes the materials pixel by pixel, and generates the image for displaying the result of the material decomposition (step S406). For example, the generating unit 383b calculates the density of the decomposition target material of the material decomposition for each pixel corresponding to the point at which the material decomposition is performed. The generating unit 383b uses, for example, a method to be explained later to calculate the density of the decomposition target material of the material decomposition, and generates the image.

In general, when the energy of the X-rays irradiating the subject P is denoted as E, the linear attenuation coefficient of the decomposition target material of the material decomposition as $\mu(E)$, the mass attenuation coefficient of the decomposition target material of the material decomposition as $\alpha_n(E)$, the density of the decomposition target material of the material decomposition as $\rho_n$, and the number of the decomposition target materials of the material decomposition as N, Expression (1) below is established. Expression (1) represents that the linear attenuation coefficient $\mu(E)$ is equal to the sum of the products $\alpha_n(E) \cdot \rho_n$ of the mass attenuation coefficients and the densities of the materials through which the X-rays have passed after being emitted from the X-ray tube 121 and being incident into one of the detecting elements of the detector 13.

$$\mu(E) = \sum_{n=1}^{N} \alpha_n(E) \cdot \rho_n \tag{1}$$

For example, suppose that the identifying unit 382b has identified the energy bins E20, E30, E40, E50, and E60 illustrated in FIG. 14, that is, the energy bins other than the energy bin E10, as the energy bins to be used for the material decomposition. By setting up Expression (1) for each of the energy bins E20, E30, E40, E50, and E60, and transforming Expression (1) into simultaneous equations, Expression (2) below can be obtained. In Expression (2), $E_k$ represents the energy of X-rays in the k-th energy bin (k=2, . . . , 6). Expression (2) is an expression in the case in which the materials indicated as "n=1 and 3" are the decomposition target materials of the material decomposition.

$$\begin{pmatrix} \mu(E_2) \\ \vdots \\ \mu(E_k) \end{pmatrix} = \begin{pmatrix} \alpha_1(E_2) & \alpha_3(E_2) \\ \vdots & \vdots \\ \alpha_1(E_k) & \alpha_3(E_k) \end{pmatrix} \begin{pmatrix} \rho_1 \\ \rho_3 \end{pmatrix} \tag{2}$$

The generating unit 383b calculates the densities of the decomposition target materials of the material decomposition on which the information has been obtained at step S401 by the obtaining unit 381b. For example, the generating unit 383b solves Expression (2) using a least squares method, and thus, calculates the densities of the decomposition target materials on which the information has been obtained by the obtaining unit 381b. The generating unit 383b then generates, for example, an image indicating the calculated densities of the decomposition target materials. The generating unit 383b may use, for example, a weighted least squares method based on errors normalized by the number of photons in the energy bins or a robust estimation method, instead of the least squares method. The above explanation has exemplified the method of analytically calculating the densities of the decomposition target materials on which the information has been obtained by the obtaining unit 381b. The generating unit 383b may, however, numerically calculate the densities of the materials on which the information has been obtained by the obtaining unit 381b.

Further alternatively, the generating unit 383b may use Expression (2) under constraint conditions in the spatial directions and calculate the densities of the decomposition target materials on which the information has been obtained by the obtaining unit 381b. Examples of the constraint conditions in the spatial directions include, but are not limited to, structural information obtained from the total energy reconstructed image. In the total energy reconstructed image, if a region possibly includes the same tissue, such as a vascular wall, or the same material, such as air, the densities of the decomposition target materials in the region are expected to have nearly the same value. Accordingly, using Expression (2) under the constraint conditions in the spatial directions allows accurate calculation of the densities of the decomposition target materials of the material decomposition. If, for example, a region possibly includes the same tissue, such as a vascular wall, or the same material, such as air, the density of a certain decomposition target material at a point corresponding to a certain pixel in the region may be set to the density of a decomposition target material at a point corresponding to a pixel adjacent to the certain pixel. The constraint conditions in the spatial directions and constraint conditions in the energy direction are also called regularization terms.

The above has explained the example of the process performed by the photon counting X-ray CT apparatus $1b$ according to the ninth embodiment. As described above, the obtaining unit $381b$ of the photon counting X-ray CT apparatus $1b$ according to the ninth embodiment obtains the information on the decomposition target materials for the material decomposition among the candidate decomposition target materials for the material decomposition. Specifically, the user selects the target materials of the material decomposition, and the obtaining unit $381b$ of the photon counting X-ray CT apparatus $1b$ according to the ninth embodiment obtains the selected target materials. In other words, the user narrows down the target materials to be taken into account when the generating unit $383b$ generates the image for displaying the result of the material decomposition. As a result, the photon counting X-ray CT apparatus $1b$ according to the ninth embodiment can keep the calculation results of the densities of the decomposition target materials of the material decomposition from including errors caused by materials that need not be decomposed. The photon counting X-ray CT apparatus $1b$ according to the ninth embodiment can also more accurately perform the material decomposition in accordance with the viewpoint of the user.

In the ninth embodiment, the identifying unit $382b$ identifies energy bins to be used for the material decomposition among the energy bins set along the energy of the X-rays irradiating the subject. Specifically, the identifying unit $382b$ identifies, as energy bins to be used for the material decomposition among the energy bins, a smaller number of energy bins than the total number of the energy bins, in the descending order of the energy. Alternatively, the identifying unit $382b$ identifies, as energy bins to be used for the material decomposition among the energy bins, energy bins that do not overlap the K absorption edge of the decomposition target materials. That is, the identifying unit $382b$ identifies, as the energy bins to be used for the material decomposition, energy bins that facilitate the contrast between the decomposition target materials of the material decomposition. As a result, the photon counting X-ray CT apparatus $1b$ according to the ninth embodiment can accurately perform the material decomposition.

Tenth Embodiment

In the ninth embodiment, at step S13 in FIG. 15, the user selects decomposition target materials of the material decomposition. The obtaining unit $381b$ obtains the selection result. The obtaining unit $381b$, however, may automatically obtain the decomposition target materials of the material decomposition. The following explains a tenth embodiment. In the tenth embodiment, at step S13 in FIG. 15, the obtaining unit $381b$ calculates the density of candidate decomposition target materials of the material decomposition for the pixels in each of images, the images each having the same size as that of each smoothed-reconstructed image, the pixels each having the same size as that of each pixel in the smoothed-reconstructed images, the same number of the pixels being arranged in the images along the first direction and the second direction, and obtains information on the decomposition target materials of the material decomposition on the basis of the calculation result. Note that, the explanations on the same matters as those of the ninth embodiment will be omitted.

Figure 20:
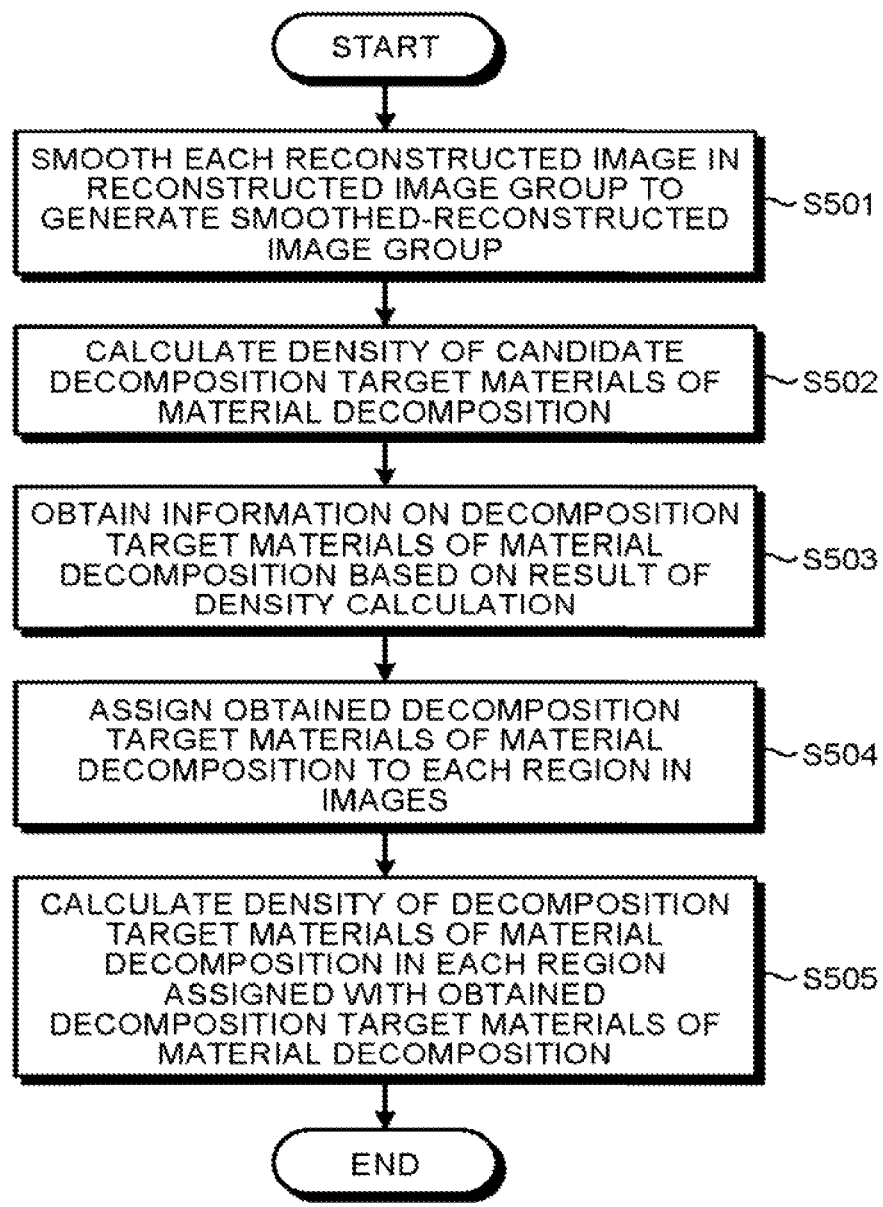
FIG. 20 is a flowchart of a procedure carried out at step S13 of FIG. 15 in the second embodiment.
Figure 21:
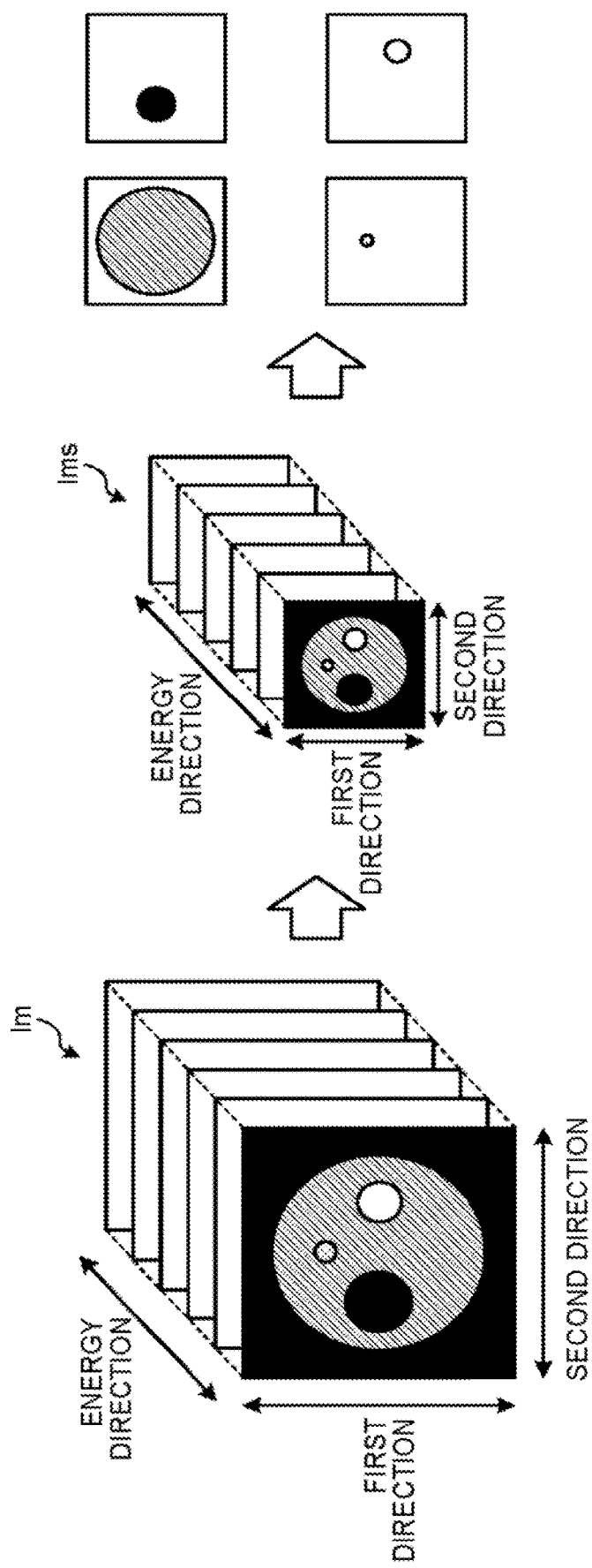
FIG. 21 is a drawing for explaining a method in which an obtaining unit obtains information on the decomposition target materials of the material decomposition.

The photon counting X-ray CT apparatus according to the tenth embodiment will be explained with reference to FIG. 20 and FIG. 21. FIG. 20 is a flowchart of a procedure carried out at step S13 in FIG. 15 in the tenth embodiment. FIG. 21 is a drawing for explaining a method in which the obtaining unit $381b$ obtains the decomposition target materials of the material decomposition in the tenth embodiment.

In the tenth embodiment, the obtaining unit $381b$ obtains information on a decomposition target material on the basis of information on decomposition target material to be subjected to the material decomposition, that is, information derived from reconstructed images that are obtained by reconstructing the pieces of projection data on a plurality of energy bins. Where the information means, for example, the type, the amount, and the density of the candidate decomposition target materials of the material decomposition. In addition, the obtaining unit $381b$ obtains information on decomposition target materials on the basis of information derived from smoothed-reconstructed images that are obtained by smoothing the reconstructed images. Furthermore, the obtaining unit $381b$ smooths the reconstructed images at least in spatial directions or in an energy direction. The specific examples thereof will be described below.

The obtaining unit $381b$ smooths the reconstructed images in the reconstructed image group Im to generate a smoothed-reconstructed image group Ims (step S501, the left drawing in FIG. 21 and the center drawing in FIG. 21). Specifically, the obtaining unit $381b$ smooths the reconstructed images in the reconstructed image group Im in the spatial directions. More specifically, the obtaining unit $381b$ smooths the reconstructed images in the reconstructed image group Im in a first direction and a second direction. First, the obtaining unit $381b$ calculates, for example, the sum of luminance values and the average value of the pixels adjacent in the first direction and the second direction in the reconstructed images in the reconstructed image group Im. In addition, the obtaining unit $381b$ assigns, for example, the calculated sum of the luminance values and the average value of the adjacent pixels to the pixels in each of images, the images each having the lengths in the first direction and the second direction that are halves of each reconstructed image, the pixels each having the same size as that of each pixel in the reconstructed images, the same number of the pixels being arranged in the images along the first direction and the second direction. Through the processing, as illustrated in FIG. 21, the lengths in the first direction and the second direction of each smoothed-reconstructed image of the smoothed-reconstructed image group Ims become halves of the lengths in the first direction and the second direction of each reconstructed image in the reconstructed image group Im. As illustrated in the center drawing in FIG. 21, the smoothed-reconstructed image group Ims includes the smoothed-reconstructed images corresponding to the energy bin E10, the energy bin E20, the energy bin E30, the energy bin E40, the energy bin E50, and the energy bin E60.

Note that a method that the obtaining unit $381b$ uses to smooth is not limited to a certain method. For example, the obtaining unit $381b$ can smooth the reconstructed images in the reconstructed image group Im using, for example, a moving average filter, a Gaussian filter, a linear filter such as a bilinear filter and a bicubic filter, a median filter, and an anisotropic filter. In addition, the obtaining unit 381*b* may smooth the reconstructed images in the energy direction. Furthermore, the obtaining unit 381*b* may perform a spatial direction smoothing and the energy direction smoothing on the reconstructed images. Note that when the reconstructed images are smoothed in the spatial directions, the size of each smoothed-reconstructed image in the smoothing direction becomes smaller than that of each reconstructed image, however, when the reconstructed images are smoothed in the energy direction, the size of each smoothed-reconstructed image is the same as that of the reconstructed images. When the reconstructed images in the reconstructed image group Im are smoothed in the spatial directions, the spatial resolution decreases, on the other hand, the precision of the material decomposition improves. When the reconstructed images in the reconstructed image group Im are smoothed in the energy direction, the energy resolution decreases, on the other hand, the precision of the material decomposition improves.

The obtaining unit 381*b* calculates the density of the candidate decomposition target materials of the material decomposition for the pixels in each of images, the images each having the same size as that of each smoothed-reconstructed image, the pixels each having the same size as that of each pixel in the smoothed-reconstructed images, the same number of the pixels being arranged in the images along the first direction and the second direction (step S502, the right diagram on FIG. 21). For example, the obtaining unit 381*b* calculates the density of the candidate decomposition target materials of the material decomposition by the following method.

The obtaining unit 381*b* formularizes above-mentioned Formula (1) in accordance with the energy bins and the candidate decomposition target materials of the material decomposition with respect to the smoothed-reconstructed image group Ims and sets the formulae, thereby obtaining Formula (3) as follows:

[Formula 3]

$$\begin{pmatrix} \mu(E_2) \\ \square \\ \mu(E_k) \end{pmatrix} = \begin{pmatrix} \alpha_1(E_1) & \square & \alpha_n(E_1) \\ \square & \square & \square \\ \alpha_1(E_k) & \square & \alpha_n(E_k) \end{pmatrix} \begin{pmatrix} \rho_1 \\ \square \\ \rho_n \end{pmatrix} \quad (3)$$

The obtaining unit 381*b* calculates the density of the candidate decomposition target materials of the material decomposition by Formula (3). The method that the obtaining unit 381*b* uses to solve Formula (3) is the same as the method that the generating unit 383*b* in the ninth embodiment uses to solve Formula (2).

The obtaining unit 381*b* obtains the information on the decomposition target materials of the material decomposition on the basis of the result of density calculation at step S502 (step S503). For example, the obtaining unit 381*b* obtains ones among the candidate target materials of the material decomposition, the obtained candidates having the highest calculated density to the n-th highest calculated density as the decomposition target materials of the material decomposition for the pixels in each of images, the images each having the same size as that of each smoothed-reconstructed image, the pixels each having the same size as that of each pixel in the smoothed-reconstructed images, the same number of the pixels being arranged in the images along the first direction and the second direction in the smoothed-reconstructed images. Where n is a natural number.

The obtaining unit 381*b* assigns the obtained decomposition target materials of the material decomposition to each region in the images, the images each having the same size as that of each reconstructed image, the regions each being obtained by enlarging the pixels in each smoothed-reconstructed image by the magnification for enlarging each smoothed-reconstructed image as large as each reconstructed image that are arranged in the first direction and the second direction in each image without gaps (step S504). Note that, a region assigned with the obtained decomposition target materials of the material decomposition includes a plurality of sub-regions each having the same size as that of each pixel in each smoothed-reconstructed image. Note that, in the tenth embodiment, the region assigned with the obtained decomposition target materials of the material decomposition has the size as large as the four pixels in each smoothed-reconstructed image that are arranged two by two along the first direction and the second direction.

The obtaining unit 381*b* calculates the density of the decomposition target materials of the material decomposition in each region assigned with the obtained decomposition target materials of the material decomposition (step S505). The obtaining unit 381*b* formularizer a formula similar to above-mentioned Formula (2) in accordance with the energy bins and the decomposition target materials of the material decomposition identified by the identifying unit 382*b* and calculates the density of the decomposition target materials of the material decomposition using the formula. The method that the obtaining unit 381*b* uses to solve the above-mentioned formula is the same as the method that the obtaining unit 381*b* in the ninth embodiment uses to solve Formula (2).

In the above-described method, the obtaining unit 381*b* calculates the density of the decomposition target materials of the material decomposition for the regions in each of the images, the images each having the same size as that of each reconstructed image, the regions each being obtained by enlarging the pixels in each smoothed-reconstructed image by the magnification for enlarging each smoothed-reconstructed image as large as each reconstructed image that are arranged in the first direction and the second direction in each image without gaps. The following steps are the same as those of the ninth embodiment.

An example of the processing performed on the photon counting X-ray CT apparatus 1*b* according to the tenth embodiment is as explained above. As described above, in the tenth embodiment, the obtaining unit 381*b* narrows down targets that the generating unit 383*b* takes into consideration to generate an image of the result of the material decomposition to be displayed, on the basis of the density of the candidate decomposition target materials of the material decomposition calculated for the pixels in each of images, the images each having the same size as that of each smoothed-reconstructed image, the pixels each having the same size as that of each pixel in the smoothed-reconstructed images, the same number of the pixels being arranged in the images along the first direction and the second direction. Thus, the photon counting X-ray CT apparatus 1*b* according to the tenth embodiment can prevent the error due to a material that need not to be subjected to the material decomposition from being included in the result of density calculation on the decomposition target materials of the material decomposition. In addition, the photon counting X-ray CT apparatus 1*b* according to the tenth embodiment can obtain a material to be subjected to the material decomposition without bothering the user.

The obtaining unit 381b generates the smoothed-reconstructed image group Ims by smoothing the reconstructed image group Im, therefore the generated images have reduced noise. The obtaining unit 381b derives the information on the candidate decomposition target materials of the material decomposition from each smoothed-reconstructed image in the smoothed-reconstructed image group Ims having reduced noise, and obtains the information on decomposition target material on the basis of the derived information. Thus, the photon counting X-ray CT apparatus 1b according to the tenth embodiment can perform the material decomposition in a high precision.

In the ninth embodiment and the tenth embodiment, the methods to perform the material decomposition with the data processing unit 38b on the basis of the reconstructed image are described. However, the data processing unit 38b can perform the material decomposition from the projection data directly. For example, the photon counting X-ray CT apparatus 1b capable of performing photon counting CT imaging can perform the material decomposition from the projection data directly by a method described below.

In a case where the material decomposition is directly performed on projection data, the obtaining unit 381b obtains information on decomposition target material on the basis of information determined from the projection data on a plurality of energy bins. Where the information means, for example, the type, the amount, and the density of candidate decomposition target materials of the material decomposition. In addition, the obtaining unit 381b obtains information on decomposition target material on the basis of information determined from the pieces of smoothed projection data that are obtained by smoothing the pieces of projection data in the energy bins. Furthermore, the obtaining unit 381b smooths the pieces of the projection data at least in a view direction, a channel direction, or the energy direction. The specific examples thereof will be described below.

The obtaining unit 381b smooths the projection data in the projection data group PJ depicted in FIG. 16 to generate the smoothed projection data group. Specifically, the obtaining unit 381b performs one or both of the spatial direction smoothing and the energy direction smoothing on the projection data in the projection data group PJ. More specifically, the obtaining unit 381b smoothes each piece of the projection data in the projection data group PJ in at least one direction of a view direction, a channel direction, or the energy direction. The method that the obtaining unit 381b uses to perform smoothing is the same as the above-described method.

When $C_0$ is the number of X-ray photons emitted to the subject P, C is the number of X-ray photons detected by the detecting element, E is the energy of X-ray, $E_k$ is the energy of the X-ray in the k-th energy bin (k=1, 2, . . . , 6), m is the number of the decomposition target materials of the material decomposition, $\mu_j$ is the linear attenuation coefficient of each decomposition target material, and $L_j$ is the X-ray absorption path length of each decomposition target material, in general, the following Formula (4) is established. Note that, the X-ray is emitted from the X-ray tube 121, permeates the subject P, and enters the detecting element of the detector 13, where the X-ray absorption path length of the decomposition target materials of the material decomposition is the total permeation distance of the X-ray permeating areas including the decomposition target material of the material decomposition.

[Formula 4] $$C(E)=C0(E)\exp^{-\Sigma_{j=1}^m \mu_j(E) L_j} \quad (4)$$

Formula (4) is formularized in each of the energy bin E10, the energy bin E20, the energy bin E30, the energy bin E40, the energy bin E50, and the energy bin E60 illustrated in FIG. 14, and setting up the formulae produces Formula (5) mentioned below:

[Formula 5]

$$\begin{pmatrix} lnC_0(E_1) - lnC(E_1) \\ \vdots \\ lnC_0(E_1) - lnC(E_k) \end{pmatrix} = \begin{pmatrix} \mu_1(E_1) & \cdots & \mu_n(E_1) \\ \vdots & \ddots & \vdots \\ \mu_1(E_k) & \cdots & \mu_n(E_k) \end{pmatrix} \begin{pmatrix} L_1 \\ \vdots \\ L_n \end{pmatrix} \quad (5)$$

where, $E_k$ indicates the energy of X-ray in the k-th energy bin (k=1, 2, . . . , 6) in Formula (5).

The obtaining unit 381b calculates X-ray absorption path lengths of the candidate decomposition target materials of the material decomposition with Formula (5). The method that the obtaining unit 381b uses to solve Formula (5) is the same as the method that the generating unit 383b in the ninth embodiment uses to solve Formula (2).

The steps following the reconstruction of the X-ray absorption path length and the density calculation of the decomposition target material performed by the obtaining unit 381b are the same as step S503 to step S505.

In addition, the following sequence may be iterated two or more times: the controlling unit 39b controls the obtaining unit 381b to obtain the information on the decomposition target material, controls the identifying unit 382b to identify the energy bin to be used in the material decomposition, controls the generating unit 383b to perform the material decomposition using the projection data having the energy bin identified with the identifying unit 382b, and generate an image for displaying the result of the material decomposition. Alternatively, the following sequence may be iteratively performed two or more times: the controlling unit 39b controls the obtaining unit 381b to obtain the information on the decomposition target material, controls the generating unit 383b to perform the material decomposition using the projection data having the energy bin identified with the identifying unit 382b, and generates an image for displaying the result of the material decomposition. In this case, the identification of the energy bin to be used in the material decomposition in the identifying unit 382b is performed before the iteration of the above-mentioned sequence.

The iteration of the sequence mentioned above can be applied to the above-described embodiments. Furthermore, the controlling unit 39b may iterate the following processing: causing the data processing unit 38b to calculate the density of the candidate decomposition target materials of the material decomposition with Formula (3) or Formula (5) mentioned above; causing the display unit 32 to display the result of density calculation; prompting the user to select the decomposition target materials of the material decomposition on the basis of the result of density calculation; and performing step S403 to step S406 depicted in FIG. 18.

By iterating the processing, the controlling unit 39b can narrow down the targets that the generating unit 383b takes into consideration to generate an image of the result of the material decomposition to be displayed. Thus, the photon counting X-ray CT apparatus 1b can prevent the error due to a target that need not to be subjected to the material decomposition from being included in the result of density calculation on the decomposition target materials of the material decomposition. As a result, the photon counting X-ray CT apparatus 1b can perform the material decomposition in a high precision.

Note that, the obtaining unit 381b may apply steps S502 to S505 mentioned above to the reconstructed images in the reconstructed image group Im, without smoothing the reconstructed images in the reconstructed image group Im. In this case, for example, calculating the density of the candidate decomposition target materials of the material decomposition, obtaining the information on the decomposition target materials of the material decomposition, and assigning the decomposition target materials of the material decomposition are performed for the pixels in each of images, the images each having the same size as that of each reconstructed image, the pixels each having the same size as that of each pixel in the reconstructed images, the same number of the pixels being arranged in the images along the first direction and the second direction. Although in the case where steps S502 to S505 are applied to the reconstructed images in the reconstructed image group Im, the obtaining unit 381b can narrow down the targets that the generating unit 383b takes into consideration to generate an image of the result of the material decomposition to be displayed.

Furthermore, in the photon counting X-ray CT apparatus 1b according to the tenth embodiment, the obtaining unit 381b may have calculated the density of each of the candidate decomposition target materials with respect to all combinations of the candidate decomposition target materials of the material decomposition, and may switch images indicating the results of the material decomposition to be displayed on the display unit 32 in accordance with a user request.

In addition, the method of the material decomposition described above can be executed on a photon counting X-ray CT apparatus that includes the detector having a detecting element configured to detect the intensity of X-ray emitted to the subject and collects the projection data at different energy levels using three or more different tube voltages. In this case, the projection data and the reconstructed image corresponding to each X-ray tube voltage can be obtained, instead of the projection data and the reconstructed image corresponding to the energy bins.

The obtaining unit 381b may obtain information on the decomposition target materials of the material decomposition at step S503 on the basis of an reconstructed image or the CT value of a smoothed-reconstructed image rather than the result of density calculation at S502 because the CT value is different for each material.

Next, another embodiment that is a combination of the first embodiment to the tenth embodiment will be described.

The photon counting X-ray CT apparatus 1b according to the ninth embodiment or the tenth embodiment may apply the grouping procedure according to the first embodiment to the eighth embodiment to the first energy bin identified by the identifying unit 382b. In this case, the photon counting X-ray CT apparatus 1b according to the ninth embodiment or the tenth embodiment includes a determining unit and an allocating unit similar to the determining unit 51 and the allocating unit 52, and performs the following processing.

The obtaining unit 381b obtains information on the decomposition target material to be subjected to the material decomposition among materials that can exist in a certain region within the subject from which the projection data in the plurality of first energy bins is obtained, the first energy bins being set on the energy distribution of the X-ray emitted from the X-ray tube 121.

The identifying unit 382b identifies the first energy bins to be used for the material decomposition among the first energy bins on the basis of the information on the decomposition target material. For example, the identifying unit 382b identifies the first energy bins E4 to E9 as the first energy bins to be used for the material decomposition with respect to the material A in association with the graph G11 illustrated in FIG. 5.

The data acquiring unit 14b allocates a signal to any of the first energy bins in accordance with the measured energy on the basis of the entered X-ray, acquiring the first data group that is the count data of the first energy bins.

The determining unit determines a plurality of second energy bins in which a plurality of first energy bins identified by the identifying unit 382b are grouped, in accordance with the decomposition target material the information on which is obtained by the obtaining unit 381b. For example, the determining unit may determine the second energy bin E102 in which the first energy bins E4 to E6 are grouped and the second energy bin E103 in which the first energy bins E7 to E9 are grouped, with respect to the material A in association with the graph G11 illustrated in FIG. 5.

The allocating unit generates the second data group by allocating the first data group to any of the second energy bins. The generating unit 383b generates an image of the distribution of the decomposition target material using the second data group.

With this configuration, the photon counting X-ray CT apparatus 1b according to the ninth embodiment can perform the material decomposition using the energy bin suitable for the decomposition target material obtained by the obtaining unit 381b. Thus, the photon counting X-ray CT apparatus 1b according to the ninth embodiment can perform the material decomposition in a higher precision.

In addition, the processing to be executed in the ninth embodiment or the tenth embodiment may be performed exclusively on a material selected with the user interface according to any one of the fourth embodiment to the eighth embodiment. Where the material selected with one of these user interfaces is a material that can be present somewhere in an entire imaged region, that is, in an entire image. By contrast, a material obtained by the obtaining unit 381b is a material that can exist in a certain region in the imaging region. With this configuration, the photon counting X-ray CT apparatus 1b according to the ninth embodiment or the tenth embodiment can narrow down materials on which the processing in the ninth embodiment or the tenth embodiment is subjected, using the user interface according to any one of the fourth embodiment to the eighth embodiment. Consequently, the photon counting X-ray CT apparatus 1b according to the ninth embodiment or the tenth embodiment can perform the processing according to the ninth embodiment or the tenth embodiment effectively.

Finally, an embodiment other than the first embodiment to the tenth embodiment will be explained.

Although the first embodiment to the tenth embodiment describe a case in which the photon counting X-ray CT apparatus performs the various pieces of processing, embodiments are not limited to the embodiments. For example, an image processing system including the photon counting X-ray CT apparatus and an image processing apparatus may perform the above-described various pieces of processing. The image processing apparatus is, for example, a workstation, an image storage apparatus (an image server) or a viewer of a picture archiving and communication system (PACS), various apparatuses of an electronic medical recording system, or the like. In this case, for example, the photon counting X-ray CT apparatus collects the projection data, or other items. The image processing apparatus receives the projection data or other items collected by the photon counting X-ray CT apparatus from the photon counting X-ray CT apparatus or from the image server through a network or receives the pieces of data input from the user through a storage medium or the like and stores the pieces of data in the storage unit. The image processing apparatus may perform the above-described various pieces of processing on the projection data or other items stored in the storage unit.

The instruction in the processing procedure according to the first embodiment to the tenth embodiment may be executed based on a computer program that is software. A general purpose computer system stores in advance and reads the computer program, thereby achieving advantageous effects similar to the effects achieved by the photon counting X-ray CT apparatus according to the first embodiment to the tenth embodiment. The instructions described in the first embodiment to the tenth embodiment are recorded, as a computer program that can be executed by a computer, on a magnetic disk (e.g., a flexible disk, a hard disk), an optical disc (e.g., a CD-ROM, a CD-R, a CD-RW, a DVD-ROM, a DVD±R, a DVD±RW), in a semiconductor memory, or in a recording medium similar thereto. Any storage format may be used for a storage medium readable by the computer or an embedded system. The computer reads the computer program from the recording medium and causes the CPU to implement the instructions described in the computer program based on the computer program. This achieves the same operation as the photon counting X-ray CT apparatus according to the first embodiment to the tenth embodiment. The computer may read or load the computer program via a network.

Some of the above-described processes to achieve the first embodiment to the tenth embodiment may be executed by the operating system (OS) running on the computer based on the computer program installed from the storage medium in a computer or an embedded system, or middleware (MW) such as database management software and a network. Furthermore, the storage medium is not limited to those media independent from a computer or an embedded system. Those media may be used that store or temporally store a computer program downloaded over a local area network (LAN) or the Internet, for example. The number of storage media is not limited to one. A plurality of storage media may be used for executing the processes according to the first embodiment to the tenth embodiment and are included in the storage media for the first embodiment to the tenth embodiment. That is, one or more storage media may be configured in the embodiments.

The computer or the embedded system in the embodiments executes the processes according to the above-described embodiments, based on the computer program stored in the storage medium. The computer or the embedded system may be a single apparatus such as a personal computer and a microcomputer. Alternatively, the computer or the embedded system may be a system in which a plurality of devices are coupled to each other through a network. The computer in the embodiments is not limited to a personal computer and it may include an operation processing unit and a microcomputer included in an information processing unit. That is, the computer in the embodiments is a general term for devices and apparatuses capable of achieving the functions according to the embodiments through the computer program.

Figure 22:
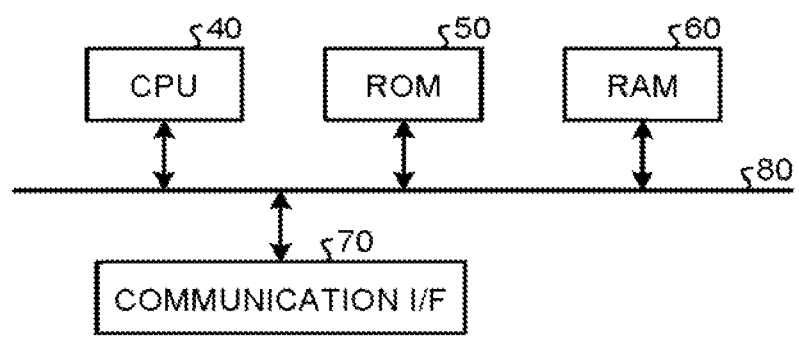
FIG. 22 is a diagram of a hardware configuration of an image processing apparatus according to an embodiment other than the first and second embodiments.

FIG. 22 is a schematic diagram of an example of a hardware configuration of the image processing apparatus according to the embodiments other than the first embodiment to the tenth embodiment. The image processing apparatus according to the first embodiment to the tenth embodiment includes a controller such as a central processing unit (CPU) 40, memories such as a read-only memory (ROM) 50 and a random access memory (RAM) 60, a communication interface (I/F) 70 for connecting to a network and establishing communications, and a bus 80 for connecting each of these units.

The computer program executed on the image processing apparatus according to the first to the tenth embodiments is provided incorporated in the ROM 50 or the like in advance. The computer program executed on the image processing apparatus according to the first to the tenth embodiments can cause a computer to function as the units included in the image processing apparatus. In the computer, the CPU 40 can read the computer program from a computer-readable storage medium onto a main memory, and execute the computer program.

As explained above, according to the embodiments, it is possible to perform the material decomposition in a high precision.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A photon counting X-ray CT apparatus comprising:
an X-ray tube that generates X-rays;
a detector including a plurality of detecting elements configured to output signals based on incident X-rays; and
processing circuitry configured to
obtain information on decomposition target materials to be decomposed among materials possible to be present in a certain region in a subject from which projection data of a plurality of first energy bins set on an energy distribution of the X-rays emitted from the X-ray tube has been acquired, the information on the decomposition target materials being obtained based on information derived from a plurality of reconstructed images obtained by reconstructing respective pieces of the projection data of the plurality of first energy bins,
identify, based on the information on the decomposition target materials, a set of energy bins to be used for material decomposition among the plurality of first energy bins set on the energy distribution of the X-rays,
use the projection data of the identified set of energy bins to perform the material decomposition, and
generate an image for displaying a result of the material decomposition, wherein the processing circuitry calculates a density of candidate decomposition target materials that are the materials possible to be present in the certain region and obtains materials having a highest calculated density to an n-th highest calcu- lated density as the information on the decomposition target materials, n being a natural number.

2. The photon counting X-ray CT apparatus according to claim 1, wherein the
processing circuitry obtains the information on the decomposition target materials based on information derived from a plurality of smoothed reconstructed images obtained by smoothing the plurality of reconstructed images.

3. The photon counting X-ray CT apparatus according to claim 2, wherein the processing circuitry smooths the plurality of reconstructed images in at least one of spatial directions and an energy direction.

4. A photon counting X-ray CT apparatus comprising:
an X-ray tube that generates X-rays;
a detector including a plurality of detecting elements configured to output signals based on incident X-rays; and
processing circuitry configured to
obtain information on decomposition target materials to be decomposed among materials possible to be present in a certain region in a subject from which projection data of a plurality of first energy bins set on an energy distribution of the X-rays emitted from the X-ray tube has been acquired, the information on the decomposition target materials being obtained based on information derived from the projection data of the plurality of first energy bins,
identify, based on the information on the decomposition target materials, a set of energy bins to be used for the material decomposition among the plurality of first energy bins set on the energy distribution of the X-rays,
use the projection data of the identified set of energy bins to perform the material decomposition, and
generate an image for displaying a result of the material decomposition, wherein the processing circuitry calculates density of candidate decomposition target materials that are the materials possible to be present in the certain region and obtains materials having a highest calculated density to an n-th highest calculated density as the information on the decomposition target materials, n being a natural number.

5. The photon counting X-ray CT apparatus according to claim 4, wherein the processing circuitry obtains the information on the decomposition target materials based on information derived from a plurality of pieces of smoothed projection data obtained by smoothing respective pieces of the projection data of the first energy bins.

6. The photon counting X-ray CT apparatus according to claim 5, wherein the processing circuitry smooths the projection data of the first energy bins in at least one of a viewing direction, a channel direction, and an energy direction.

* * * * *